United States Patent [19]
de la Torre et al.

[11] Patent Number: 5,716,368
[45] Date of Patent: Feb. 10, 1998

[54] KNOTMAKER WITH CURVED ELONGATE MEMBER USED IN TYING A LIGATURE

[75] Inventors: Roger A. de la Torre, Lake St. Louis; James Stephen Scott, St. Charles, both of Mo.; James E. Jerivs, Atherton; Kenneth H. Mollenauer, Santa Clara, both of Calif.

[73] Assignee: General Surgical Innovations, Inc., Cupertino, Calif.

[21] Appl. No.: 479,169

[22] Filed: Jun. 7, 1995

Related U.S. Application Data

[63] Continuation-in-part of Ser. No. 277,987, Jul. 20, 1994, Pat. No. 5,527,323, which is a continuation-in-part of Ser. No. 71,297, Jun. 2, 1993, Pat. No. 5,391,176.

[51] Int. Cl.$^6$ ........................................ A61B 17/00
[52] U.S. Cl. ........................ 606/148; 606/139; 289/17; 112/169
[58] Field of Search ........................ 606/139, 141, 606/144, 145, 148; 112/169, 80.03; 289/17

[56] References Cited

U.S. PATENT DOCUMENTS

| | | |
|---|---|---|
| 2,566,625 | 9/1951 | Nagelmann . |
| 4,641,652 | 2/1987 | Hutterer et al. . |
| 5,026,379 | 6/1991 | Yoon . |
| 5,129,912 | 7/1992 | Noda et al. . |
| 5,217,470 | 6/1993 | Weston . |
| 5,234,443 | 8/1993 | Phan et al. . |
| 5,250,054 | 10/1993 | Li ............................ 606/148 |
| 5,281,236 | 1/1994 | Bagnato et al. . |
| 5,312,423 | 5/1994 | Rosenbluth et al. . |
| 5,336,231 | 8/1994 | Adair ............................ 606/148 |
| 5,405,352 | 4/1995 | Weston . |
| 5,499,991 | 3/1996 | Garman et al. ............................ 606/148 |
| 5,573,542 | 11/1996 | Stevens ............................ 606/148 |
| 5,601,572 | 2/1997 | Middleman et al. ............................ 606/139 |

*Primary Examiner*—Jeffrey A. Schmidt
*Attorney, Agent, or Firm*—Howell & Haferkamp, L.C.

[57] ABSTRACT

A surgical instrument facilitates tying of a knot in a length of suture material at a remote surgical location. The instrument is comprised of an inner rod having a length of suture wrapped over the rod in a particular pattern. A needle may be secured to a free end of the suture and the pattern of wrapping the suture on the rod enables loops of suture to move off the rod end and over the needle to form a knot in the suture. The inner rod is received in an interior bore of an outer rod for manually controlled reciprocating movement therein. The inner rod is manually retracted into the interior bore of the outer rod to cause the outer rod to move the loops of suture off the inner rod end and over the needle in forming a knot in the suture. An extendable filament is contained in the inner rod and has a connector at its distal end for holding the free end of the suture. The distal end is curved, so that extending the filament from the inner rod causes it to pass the suture around and behind a tissue to be ligated where the suture may be taken from the filament by a grasper. Pairs of prongs are also provided on the distal ends of the inner and outer rods for sequentially ejecting pre-tied suture knots off the distal end of the inner rod.

18 Claims, 10 Drawing Sheets

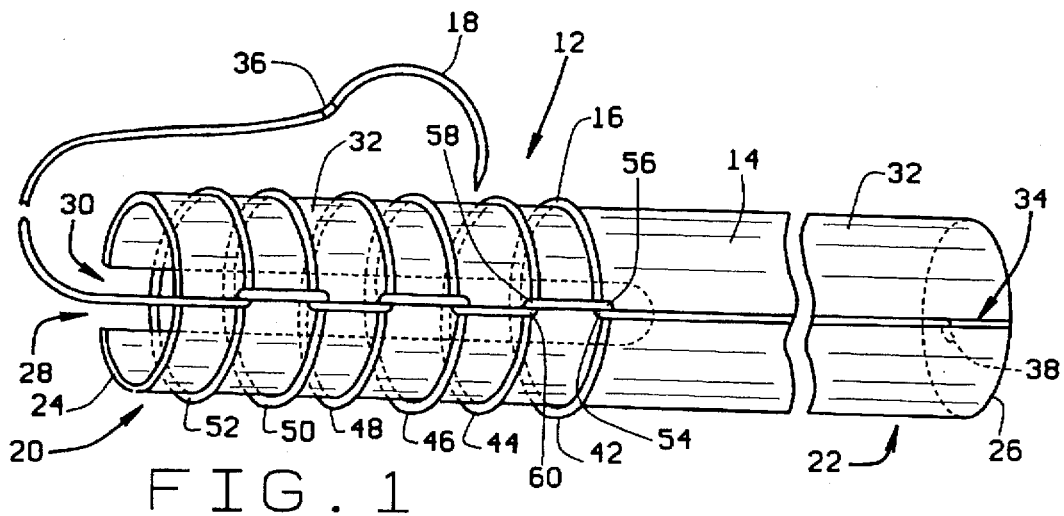
FIG. 1
FIG. 2
FIG. 3
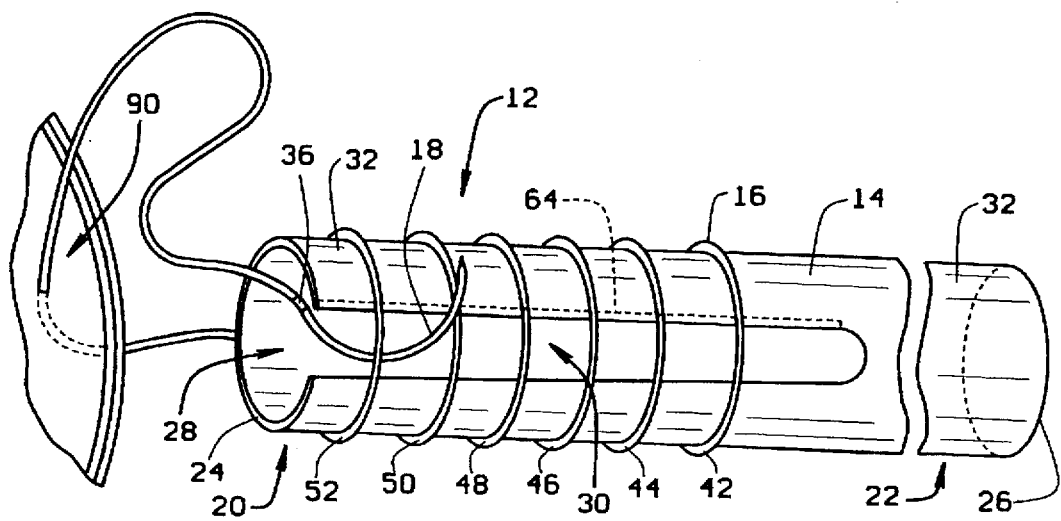
FIG. 4

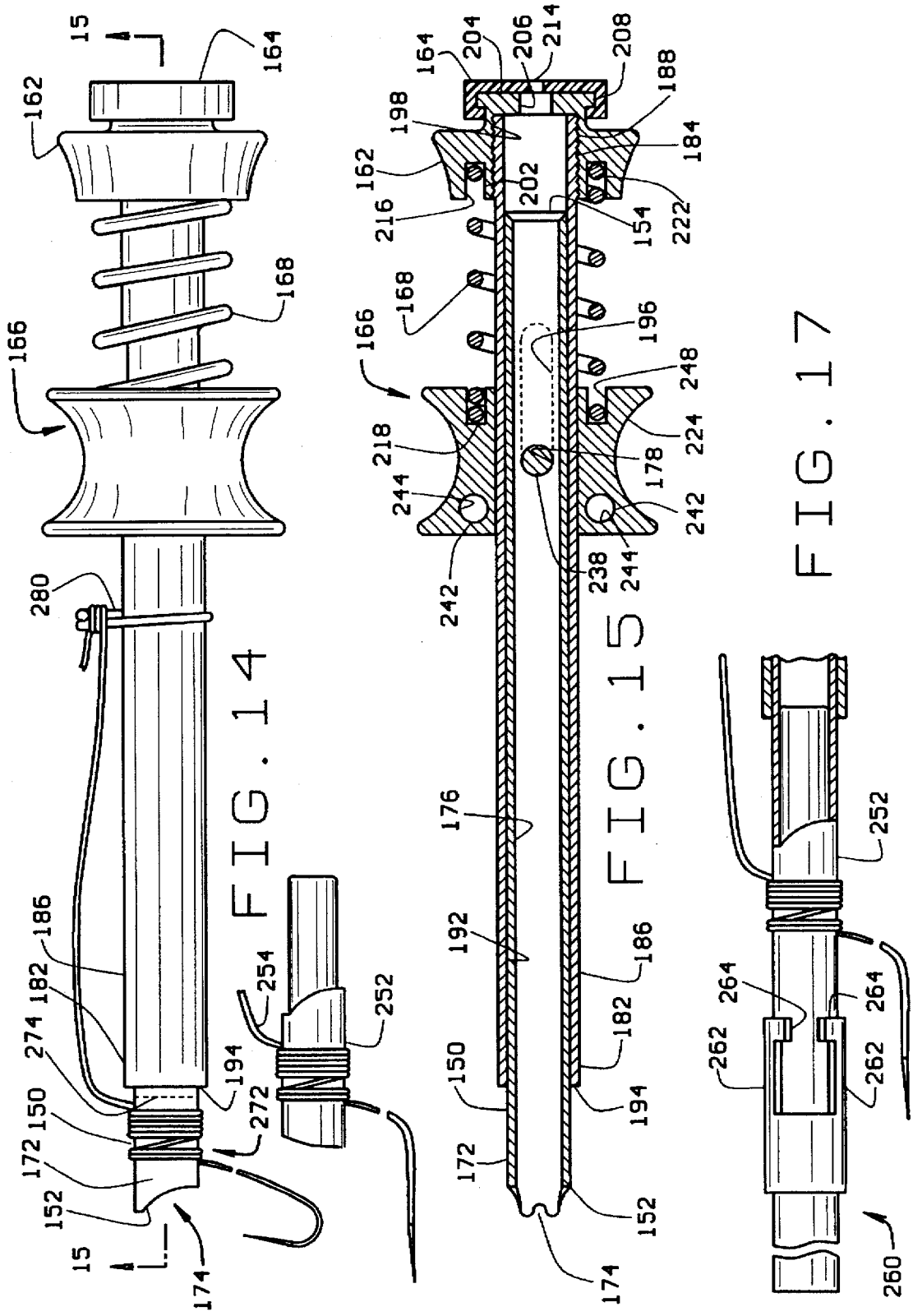

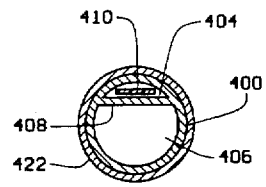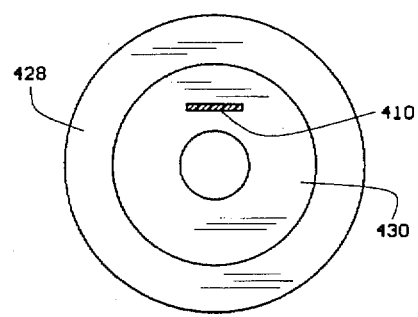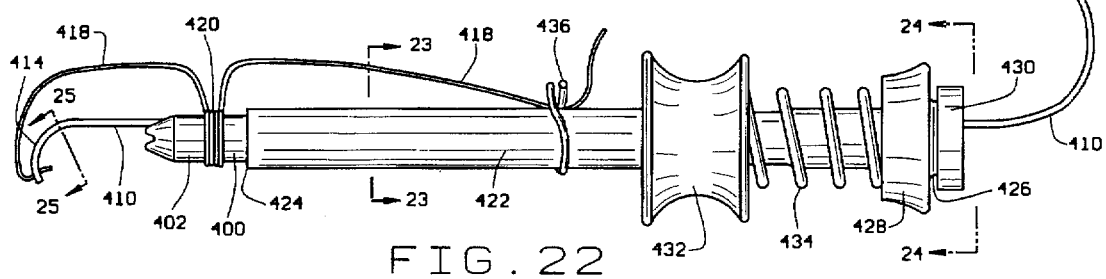

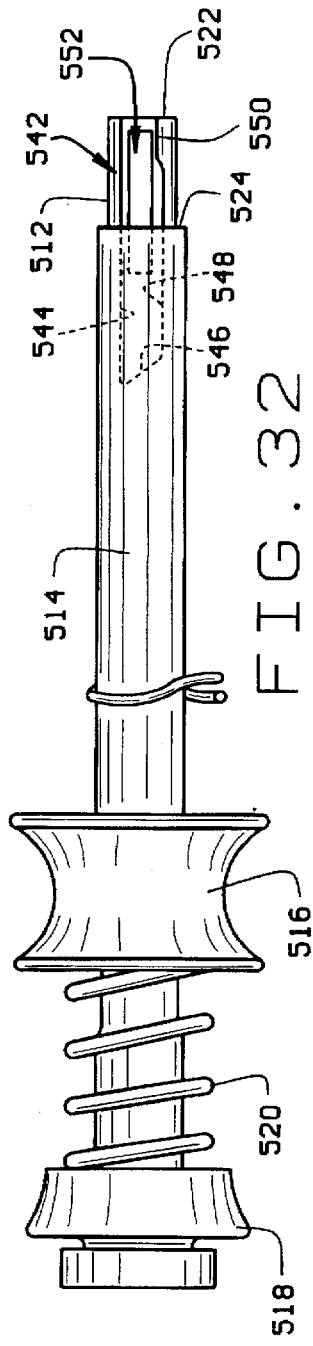
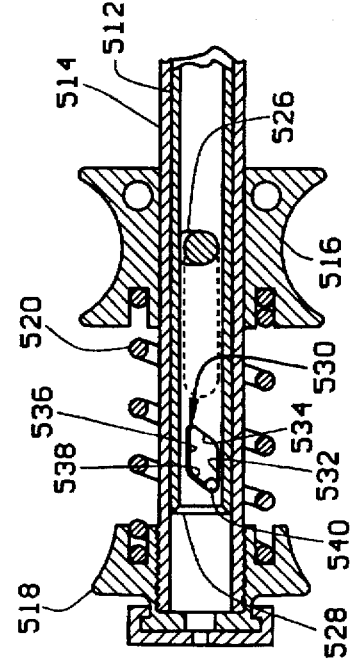
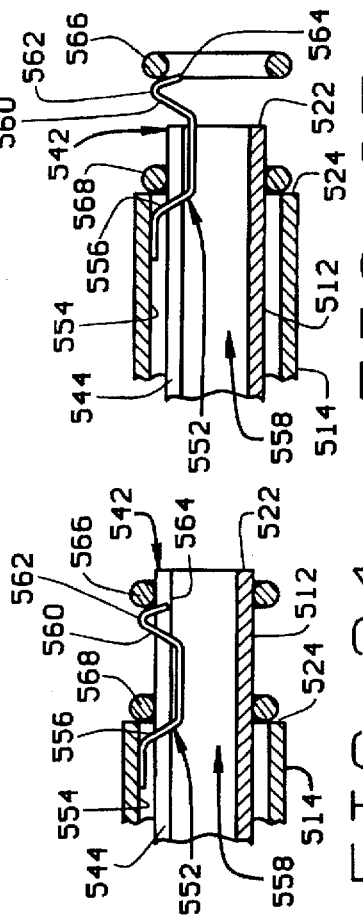
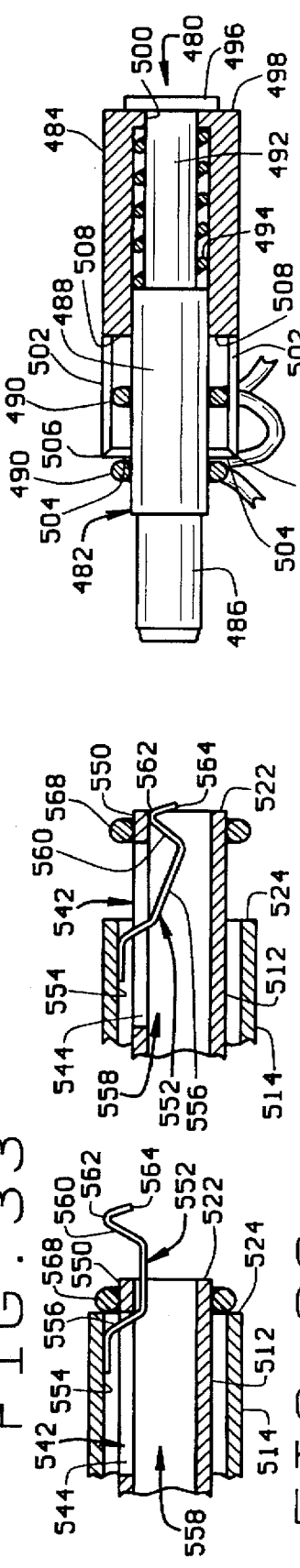

KNOTMAKER WITH CURVED ELONGATE MEMBER USED IN TYING A LIGATURE

This application is a continuation-in-part application of U.S. patent application Ser. No. 08/277,987, filed Jul. 20, 1994, now U.S. Pat. No. 5,527,323 which is a continuation-in-part application of U.S. patent application Ser. No. 08/071,297, filed Jun. 2, 1993, and now U.S. Pat. No. 5,391,176.

BACKGROUND OF THE INVENTION (1) Field of the Invention

The present invention pertains to a surgical instrument for tying a knot in a length of suture at a remote location.

(2) Description of the Related Art

Various different types of instruments are known in the prior art for use in tying knots in lengths of suture material. Many of these prior art instruments have been developed with the intent to facilitate tying knots in suture material at surgical sites located in remote areas that are difficult to access. Many prior art instruments are designed for use in surgical procedures where large, deep incisions are made into the body. The instruments enable tying knots in sutures deep in the incisions. Many prior art instruments are also designed for use in laparoscopic surgical procedures where small incisions are made and the remote surgical site is accessed through cannulas or tubes. Examples of known instruments employed in tying knots in lengths of suture material are disclosed in the U.S. Patents of Nagelmann U.S. Pat. No. 2,566,625, Larzelere U.S. Pat. No. 2,595,086, Mulhollan et al. U.S. Pat. No. 4,602,635, Hayhurst U.S. Pat. No. 4,961,741, the U.S. Patents of Li U.S. Pat. Nos. 5,084,058; 5,087,263; and 5,163,946; the U.S. Patent of Li et al. U.S. Pat. No. 5,133,723; and the U.S. Patent of Rosenbluth et al. U.S. Pat. No. 5,312,423.

A common characteristic of many known surgical knot-tying instruments is that they are very complicated to operate and time consuming to set up prior to their use. Moreover, many prior art surgical knot-tying instruments are used in a procedure that involves first tying the knot in a length of suture remote from the surgical location and then moving the loose knot along the length of suture material to a position proximate to the surgical location before the knot is tightened at the surgical location.

SUMMARY OF THE INVENTION

The present invention overcomes disadvantages commonly associated with prior art surgical knot-tying instruments by providing a simplified surgical instrument for tying a knot in a length of suture proximate to a surgical site. More specifically, the surgical instrument of the present invention may be employed in either open incision or laparoscopic surgery procedures to position a needle and a length of suture material proximate to a surgical location and to form one or more stitches with the length of suture material at the surgical location, and then to tie a knot in the length of suture material at the surgical location. Alternatively, the instrument of the invention may be used to position a length of suture at a surgical location and assist in forming a ligature in the length of suture.

A first embodiment of the instrument is basically comprised of an elongate rod having opposite first and second ends. The longitudinal length of the rod is designed to enable the first end of the rod to be inserted through a conventional, laparoscopic trocar to position the rod first end proximate to a surgical location or site within a body cavity accessible by the trocar. The second end of the rod projects from the trocar where it is grasped manually to enable manipulation of the rod first end within the body cavity. The rod has a first interior bore extending through the rod between its opposite ends, and a second interior bore that also extends through the rod between its opposite ends. An interior wall extending through the rod separates the first interior bore from the second interior bore. The second interior bore has a larger cross-sectional area than the first interior bore and is dimensioned sufficiently large to enable insertion of conventional laparoscopic surgical instruments, for example a surgical grasper, therethrough.

An elongate, flexible and resilient filament extends through the first interior bore of the rod. The filament has opposite proximal and distal ends that project from the opposite proximal and distal ends of the rod, respectively. The distal end of the filament has a slot formed therein that is dimensioned sufficiently large to receive and hold a length of suture. A portion of the filament adjacent its distal end has a curved configuration. By retracting the filament distal end into the first interior bore by pulling the proximal end of the filament from the interior bore, the bore straightens out the curvature in the distal end of the filament as it enters the bore. In extending the distal end of the filament from the interior bore by pushing the filament proximal end into the bore, the resiliency of the portion of the filament adjacent its distal end causes this portion of the filament to return to its curved configuration.

In use of this embodiment of the invention, a free end of suture is secured in the connector at the distal end of the filament. The suture then is wrapped in one or more knots on the exterior surface of the rod adjacent its distal end. From the knots wrapped in the suture, it then extends along the length of the rod toward its proximal end and is held secure by the surgeon or is secured to a clasp provided on the rod. The distal end of the filament is retracted into the first interior bore of the rod a sufficient distance so that there are no loose lengths of suture hanging from the rod distal end.

The first end of the rod is then positioned proximate to a surgical location by inserting the rod end into an open incision or by inserting the rod end through the interior of a trocar providing access to a body cavity. With the rod distal end positioned adjacent a body tissue to be ligated by the instrument, the proximal end of the filament is then inserted through the bore to cause the distal end of the filament to be extended from the distal end of the rod. The rod is positioned so that the curved portion of the filament will extend around one side and behind the tissue to be ligated and project from the opposite side of the tissue. A surgical grasper is then inserted through the second interior bore of the rod and the suture held by the filament connector is grasped by the grasper. The suture is then pulled free from the connector and through the second interior bore of the rod. The knot of suture wrapped on the distal end of the rod is then pushed off the rod and over the free end of the suture that extends around the tissue to be ligated and into the second interior bore at the distal end of the rod where the suture is held by the grasper. The knot is passed over the free length of suture to the tissue to be ligated and by pulling the ends of the suture on opposite ends of the knot, the tissue is ligated by the length of suture. The free ends of the suture may then be cut free of the ligation knot and removed from the body cavity with the instruments.

In a further embodiment of the ligating instrument, it is employed as an inner rod of a knot tying instrument of the type disclosed in the parent application which comprises concentric inner and outer rods. The outer rod has opposite proximal and distal ends and a hollow interior bore extending through the rod between its ends. The inner rod is received in the interior bore of the outer rod for reciprocating movement therein relative to the outer rod. On reciprocating movement of the inner rod, the inner rod distal end moves toward and away from the distal end of the outer rod.

The distal end of the inner rod has axial grooves formed in its exterior surface on diametrically opposite sides of the rod end. The inner rod distal end also has a pair of axial slots formed through the rod end on diametrically opposite sides of the rod end and spaced 90° from the axial grooves formed in the rod end. A pair of resilient inner prongs are secured to the interior surface of the inner rod and extend axially and radially upwardly through the axial slots to distal ends of the prongs. The distal ends of the prongs are bent back radially inwardly and extend back into the axial slots formed in the inner rod distal end. The resiliency of the inner prongs permits them to flex inwardly into the axial slots as the inner rod distal end is moved toward the outer rod distal end, and return to their positions extending radially outwardly from the axial slots as the inner rod distal end is moved away from the outer rod distal end.

The outer rod has a pair of outer prongs secured to the interior surface of the rod at its distal end. The pair of outer prongs project axially from the outer rod distal end to distal ends of the second prongs. Each of the second prongs is divided into first and second sections. The first section of each prong extends axially from the outer rod distal end and the second section of each prong extends radially away from the inner rod distal end and then radially toward the inner rod distal end. The outer rod is positioned relative to the inner rod so that the distal ends of the outer rod prongs engage in the axial grooves of the inner rod.

A length of suture material is wrapped in knots on the distal end of the inner rod. One length of suture may be employed having several knots wrapped on the inner rod from the one length of suture. Alternatively, several separate lengths of suture may be employed, each wrapped in a separate knot on the inner rod distal end. A first suture knot is wrapped on the distal end of the inner rod adjacent the distal ends of the outer rod prongs. A second and subsequent suture knots are also wrapped around the outer rod distal end but also extend around the inner prongs of the inner rod and the first sections of the outer rod outer prongs. One free end of the suture material extends from the knots on the inner rod distal end back along the length of the outer rod and is held by the surgeon or secured to a clamp on the outer rod. The opposite free end of the suture extends from the knots wrapped on the distal end of the inner rod to a needle at the end of the suture when the instrument is to be used for placing stitches, or to the free end of the suture when the instrument is to be used in ligating tissue. If used in ligating tissue, the free end of the suture extending from the knots is held securely in the slot at the distal end of the filament described earlier.

In use of the instrument, after a stitch has been placed or the free end of the suture has been passed around tissue to be ligated by extension of the filament distal end from the instrument, the free end of the suture is grasped by a surgical grasper extended through the inner rod interior bore and is pulled back through the interior bore of the inner rod. The inner rod is then reciprocated relative to the outer rod to cause the inner rod distal end to move toward the outer rod distal end. This movement of the inner rod causes the outer rod prongs to push the first suture knot off the inner rod distal end and over the length of suture drawn into the inner rod bore. This first knot is then moved along the length of suture to the stitch or tissue being ligated where it is drawn tight.

As the inner rod distal end is moved toward the outer rod distal end, the inner prongs on the inner rod are caused to flex inwardly as they pass beneath the second suture knot wrapped around the first sections of the outer rod prongs. When the inner rod prongs pass completely beneath the second knot wrapped on the outer rod prong first sections, the resiliency of the inner rod prongs causes their distal ends to move radially back up through the slots in the inner rod to positions adjacent the second knot but now on the proximal side of the second knot. Movement of the inner rod distal end away from the outer rod distal end then causes the inner rod prongs to push the second knot up over the second sections of the outer rod prongs until the second knot is positioned on the distal sides of the outer rod prongs around the distal end of the inner rod. The instrument is then prepared for placing a second knot on a length of suture by reciprocation of the inner rod in the outer rod as previously described.

The ligating instrument comprising the extendable filament may be used in conjunction with the inner and outer prongs of the knot tying instrument. Alternatively, the surgical instrument may be provided with only the ligating filament or only the knot tying prongs.

BRIEF DESCRIPTION OF THE DRAWINGS

Further objects and features of the present invention are revealed in the following detailed description of the preferred embodiments of the invention and in the drawing figures wherein:

FIG. 1 shows a fragmented perspective view of the surgical instrument for tying a knot in a length of suture;

FIG. 2 shows a partial perspective view of a variant embodiment of the instrument of the invention;

FIG. 3 shows a perspective view of a still further embodiment of the instrument of the invention;

FIG. 4 shows a fragmented perspective view similar to that of FIG. 1 with the instrument of the invention rotated 180°;

FIG. 14 shows a further embodiment of the surgical instrument of the invention;

FIG. 15 is a cross section of the instrument shown in FIG. 14 taken along the line 15—15 of FIG. 14;

FIG. 17 shows a cartridge of the invention positioned on the end of the instrument of FIG. 14.

FIGS. 22–25 show a variant embodiment of the knot tying instrument that comprises a ligating filament;

FIG. 31 is a schematic representation of a suture loading magazine used with the knot tying instrument;

FIGS. 32 and 33 show a further embodiment of the knot tying instrument; and

FIGS. 34–37 illustrate the use of the instrument of FIGS. 32 and 33.

DESCRIPTION OF THE PREFERRED EMBODIMENTS

Figure 5:
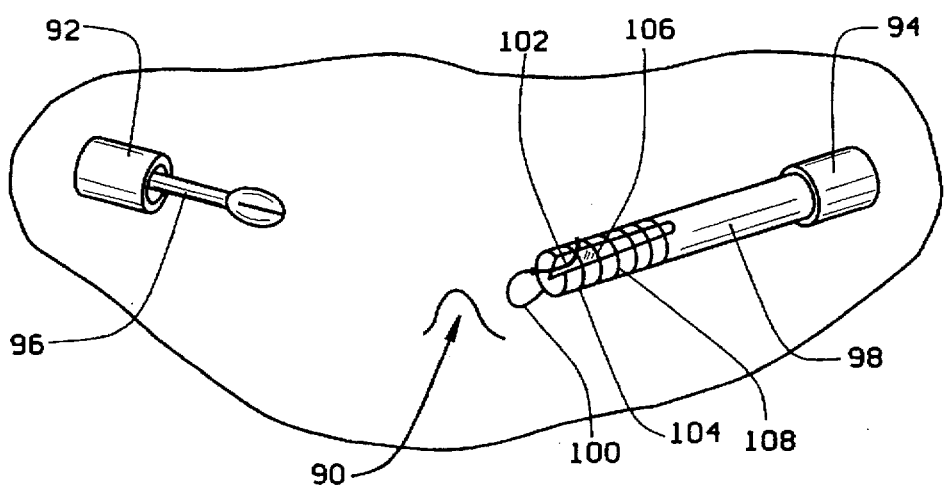
FIG. 5 is a schematic representation of a step involved in the method of use of the instrument of the invention in tying a knot in a length of suture in laparoscopic surgery.
Figure 6:
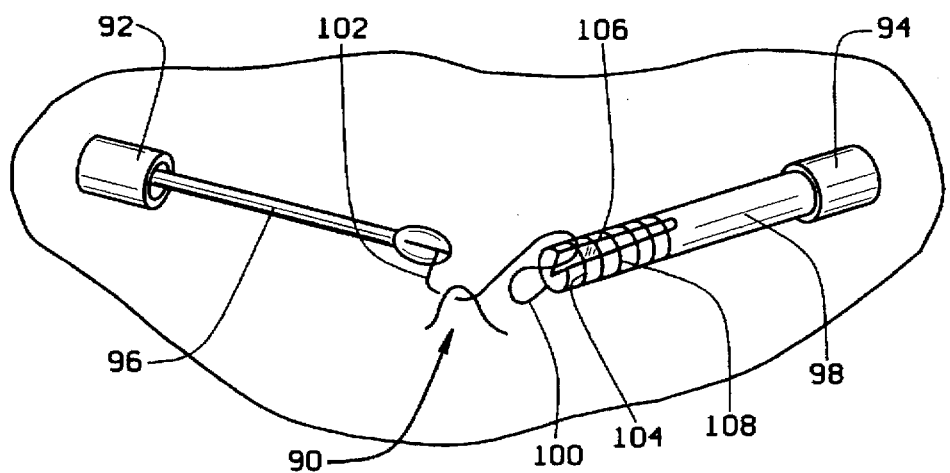
FIG. 6 is a subsequent step to that shown in FIG. 5.
Figure 7:
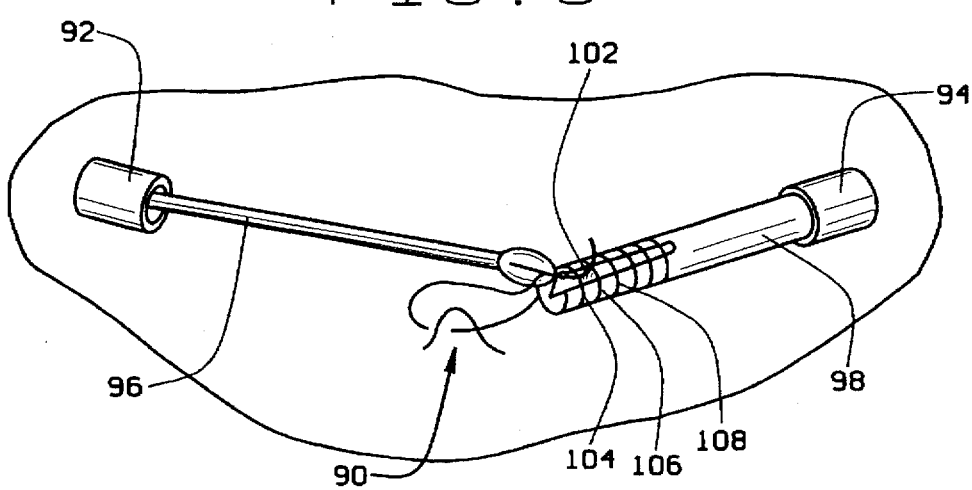
FIG. 7 is a subsequent step to that shown in FIG. 6.
Figure 8:
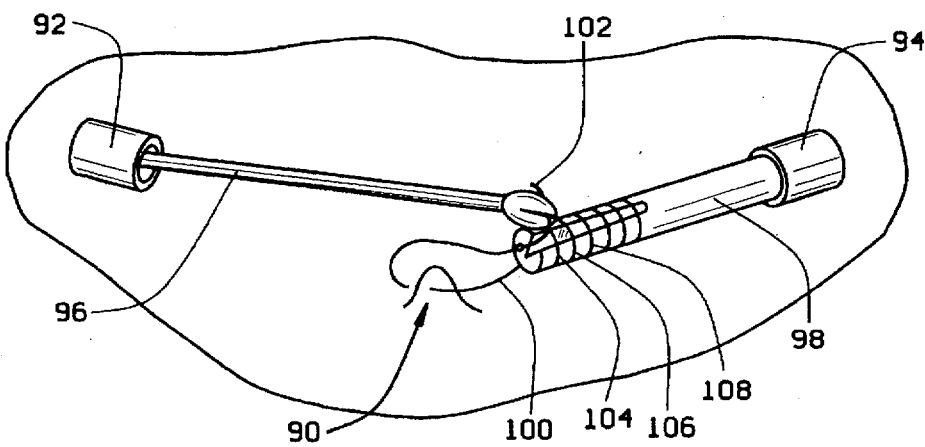
FIG. 8 is a subsequent step to that shown in FIG. 7.

A first embodiment of the surgical instrument 12 of the present invention is shown in FIGS. 1 and 4. This first to be described embodiment of the invention, as well as other embodiments of the invention yet to be described, may be constructed of any materials acceptable for use in surgical operations. The instrument is basically comprised of an elongate rod 14, a length of suture material 16 secured to the rod, and a needle 18 secured to the length of suture material.

The elongate rod has opposite first 20 and second 22 ends, or left hand and right hand ends respectively, adjacent opposite first 24 and second 26 end faces, or left and right end faces, as viewed in FIGS. 1 and 4. A hollow interior bore 28 extends longitudinally through the rod 14 between its end faces 24, 26. The interior and exterior diameter dimensions of the rod 14, as well as its longitudinal length between end faces, may vary depending on the intended application of the instrument. The instrument is designed for use with both open incision surgery and laparoscopic surgery and the rod 14 of the instrument may be dimensioned so that it can be easily inserted through the interior of a trocar in laparoscopic surgery applications. Additionally, the lateral dimensions of the instrument rod 14 may be enlarged to further facilitate its use in open incision surgical operations. The dimensions of the rod 14, suture material 16, and needle 18 shown in the drawing figures are not to scale and are not proportionate but are enlarged in FIGS. 1 and 4 to better illustrate the component parts of the invention and their relationship to each other. Moreover, it is not necessary that the instrument rod have the cylindrical configuration shown in FIGS. 1 and 4.

A slot 30 is formed through the exterior surface 32 of the rod adjacent its first end 20 forming a recess or indentation into the rod from the exterior surface to the interior bore 28. A second smaller slot 34 or slit is formed in the second end 22 of the instrument rod extending along a portion of the longitudinal length of the rod from the second end face 26.

The length of suture material 16 has opposite first 36 and second 38 ends with the first end 36 of suture material being secured to the needle 18 in a conventional manner. The total length of the suture material between its first and second ends may vary depending on the intended application of the surgical instrument of the invention, as will be explained. The second end 38 of the suture is secured adjacent the rod second end 26 by inserting the suture into the narrow slot 34. In variant embodiments of the invention, the second end 38 of the suture may be secured to the instrument rod 14 in any equivalent manner, or may be manually held adjacent the rod second end in use of the surgical instrument. The length of suture 16 extends from the instrument rod second end 22 along the exterior surface of the rod toward the rod first end 20 and is wrapped in several loops 42, 44, 46, 48, 50, 52 at the first end 20 of the rod. From the last of the plurality of loops, the suture material extends to its first end 36 secured to the needle 18.

As best seen in FIG. 1, each of the loops of suture material are wrapped around the exterior surface of the rod in a specific configuration that enables individual loops to be spaced from each other along the rod first end 20 and also enables individual loops to be manipulated to slide along the longitudinal length of the rod first end without causing adjacent loops to move along the length of the rod. Although a specific arrangement of the suture material to form the plurality of loops is shown in FIG. 1, it should be appreciated that the suture material 16 may be formed in a variety of different loop configurations on the rod first end 20 that enable the plurality of suture loops to be spaced from each other as shown in FIG. 1 and allow individual loops of suture material to be manually moved longitudinally over the exterior surface of the rod without causing adjacent loops to be moved.

The specific configuration of the suture loops shown in FIG. 1 is produced by forming a first bend 54 in the suture material 16 as it extends longitudinally over the exterior surface of the rod 14 from the second end 22 toward the first end 20 of the rod. From the first bend 54, the suture material extends laterally relative to the rod and is wrapped one complete revolution around the exterior surface of the rod back to the first bend 54. The suture material is then formed in a second bend 56 around the first bend 54 of the suture and again extends longitudinally along a portion of the rod's length, thereby completing the formation of the first loop 42 in the suture material. The subsequent or adjacent loop 44 is formed in substantially the same manner as the first described loop 42. In forming the second loop, a first bend 58 is formed in the suture material and the suture extends from the first bend laterally around the exterior surface of the rod 14 one complete revolution back to the first bend of the second loop. Next, a second bend 60 is formed in the suture material around the first bend 58 of the second loop. The suture material continues to extend longitudinally toward the rod first end 20 from the second bend 60, thereby completing the second loop 44 of suture material formed on the exterior of the rod 14. The remaining pairs of loops 46 and 48, 50 and 52, are formed in the suture material as it extends toward the rod first end 20 in the identical manner as the first pair of loops 42, 44 just described.

To illustrate that the loops of suture material formed over the exterior surface of the rod 14 may be formed in a variety of different configurations without departing from the intended scope of the claims of the invention, it is noted that the first and second loops 42, 44 are substantially mirror images of each other, and the second and third loops 44, 46 are also substantially mirror images of each other. In variations of the invention, these first three loops of suture material may have been wound around the exterior surface of the rod 14 so that their configurations are substantially identical to each other, as are the first and third loops 42, 46. Moreover, all of the loops of suture material could have been wrapped around the exterior of the rod 14 in substantially the same configuration as the first loop 42 or all of the plurality of loops could have been wrapped in substantially the same configuration as the second loop 44 without departing from the intended scope of the claimed invention and without altering the operation of the invention or its method of use.

To prevent the plurality of suture loops from unraveling from the rod first end 20 and to prevent the needle 18 from hanging free from the rod first end a strip magnet 64 is encased in the material of the rod first end extending along one side of the first slot 30 as shown in FIG. 4. By positioning the needle 18 adjacent the side of the slot 30 having the strip magnet 64, the needle is held securely in place at the rod first end 20 as shown in FIG. 4. Alternate means of securing the needle 18 at the rod first end 20 may be employed in place of the strip magnet 64.

In variant embodiments of the instrument rod 14 the strip magnet 64 could be eliminated from its position adjacent the slot 30 and the needle 18 could be held in place relative to the rod by a conventional laparoscopic surgery grasper inserted through the rod interior bore 28 from its second end 22.

FIG. 2 shows a variant embodiment of the rod 70 of the surgical instrument. In this embodiment, the rod again has a cylindrical configuration; however, the rod does not have a hollow interior bore as in the first embodiment. The rod configuration shown in FIG. 2 is solid with the slot 72 extending down into the interior of the material of the rod from the exterior surface 74. The longitudinal length of the slot 72 is determined to enable the slot to extend beneath the plurality of loops formed in suture material (not shown) wrapped over the first end of the rod 70. The remaining component parts, i.e. the suture material and needle, of the second embodiment of the surgical instrument employing the solid rod 70 are substantially identical to those of the first described embodiment of FIGS. 1 and 4.

FIG. 3 shows a still further variant embodiment of the surgical instrument rod 78. In the embodiment of the rod 78 shown in FIG. 3, the first end, or left hand end of the rod as viewed in FIG. 3, may have the same tubular configuration of the first described embodiment of FIGS. 1 and 4 or may have the solid configuration of the rod shown in FIG. 2. The rod has a slot 80 formed in its first end in the same manner as the previously described embodiments and a length of suture material is wrapped over the exterior surface of the rod and the slot with one end of the suture secured to the rod and the opposite end of the suture secured to a needle 82 in the same manner as the first described embodiments. The embodiment of FIG. 3 differs from the previously described embodiments in that the longitudinal length of the surgical instrument is divided into two sections with the first section comprising the rod 78 and the second section comprising a handle 86. As shown in FIG. 3, the second end of the rod 78 is detachably secured to one end of the handle 86 by a threaded connection 88. Other equivalent means of providing a releasable connection may also be employed. The ability of the rod 78 to be detached from the handle 86 enables the rod to be detached and disposed of after use and replaced on the handle by a like rod.

FIGS. 5–10 are schematic representations of the method of the invention employed in using the surgical instrument of the invention for tying a knot in a length of suture in a laparoscopic surgical operation. The drawing figures and their descriptions to follow only generally describe one use of the surgical instrument of the invention and are employed only to illustrate some benefits provided by the surgical instrument of the invention. Drawing FIGS. 5–10 and their descriptions to follow describe use of the surgical instrument of the invention in laparoscopic surgery forming a single stitch to close an incision. Again, it should be understood that the description to follow is illustrative only and should not be interpreted as limiting the use of the surgical instrument of the invention to only laparoscopic surgical techniques or only use in forming one stitch in securing adjacent tissues together. The benefits provided by the unique surgical instrument of the present invention suit it for use in a variety of different known surgical techniques and for use in forming both a single stitch and a line of stitching in body tissues.

FIG. 5 is a schematic representation of a view looking inside a body cavity toward an opening in a tissue 90 representing a defect to be repaired or mended by use of the surgical instrument of the invention. The drawing figure and FIGS. 6–10 to follow illustrate a laparoscopic repair of the defect 90 in the tissue and a pair of trocars 92, 94 are shown already inserted through left and right flanks of the body into the cavity, respectively. Graspers 96 are shown inserted through the left trocar 92 into the body cavity and the first end of the surgical instrument rod 98 with the length of suture 100 wrapped thereover and the needle 102 secured to the suture are shown inserted through the right trocar 94. The needle 102 is shown releasably held to the first end of the instrument rod 98 by a magnet encapsulated in the material of the rod, as was explained earlier. The length of suture extending from the needle 102 to the first suture loop 104 formed on the rod end may be longer than that shown in FIG. 5 to facilitate manipulation of the needle in producing a stitch through the defective tissue 90. The excess length of suture between the needle 102 and the first suture loop 104 may be spirally wound on the rod first end between the rod end face 106 and the first loop 104. In preparing to use the instrument of the invention, the second end of the rod 98 (not shown) extending from the exterior end of the trocar 94 is manipulated to position the rod first end proximate to the surgical location or the defective tissue 90. The graspers 96 are then used to remove the needle 102 from its magnetic attachment to the rod end and a stitch is made through the tissue defect 90 at the surgical location. Only one stitch is shown being made in FIG. 6; however, as explained earlier, the surgical instrument of the invention may be employed in forming a line of stitching to close a larger tissue defect. In forming a line of stitching, the needle and attached length of suture are passed through the tissue defect several times along the line in one direction and then are passed again through the tissue defect along a return line back to the position where the suture was first inserted through the tissue. This positions the length of suture extending to the tissue defect from the instrument rod and the length of suture extending from the tissue defect to the needle adjacent each other. With these two lengths of suture positioned adjacent each other a knot may be formed in the suture in the same manner as after forming a single stitch in the tissue defect.

Figure 9:
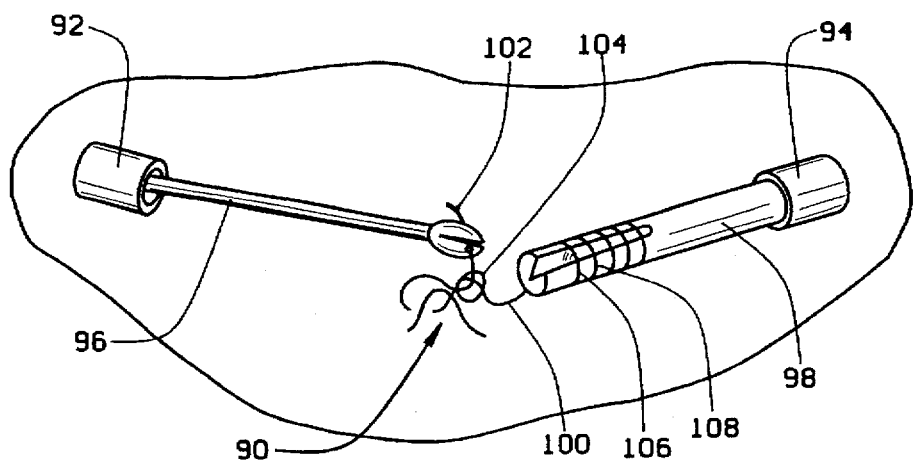
FIG. 9 is a subsequent step to that shown in FIG. 8.
Figure 10:
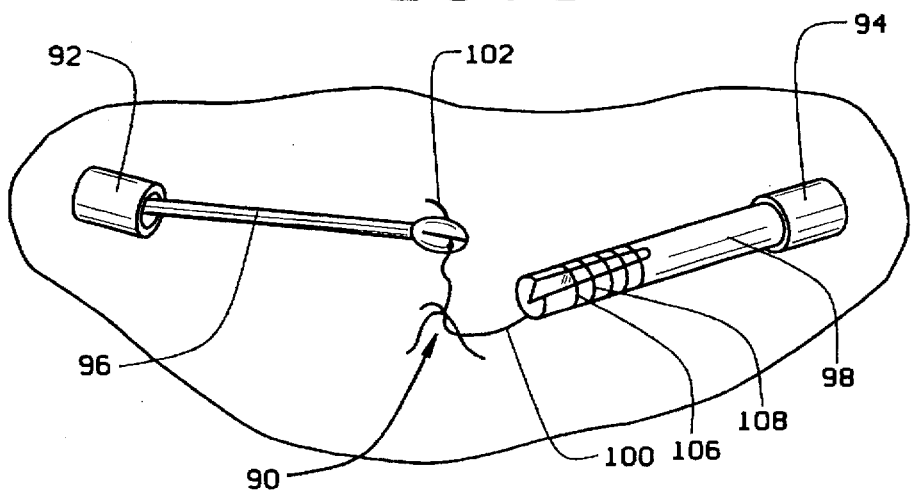
FIG. 10 is a subsequent step to that shown in FIG. 9.

In preparation to form a first throw of a knot in the suture material, the needle is repositioned by the grasper in the slot in the first rod end with the needle extending beneath the first loop 104 of suture material formed on the rod end. FIG. 4 shows in more detail the proper positioning of the needle in preparing to form the first throw of the surgical knot. The needle is held in this position beneath the first loop of the suture by the magnetism of the first rod end. The needle is then released by the grasper 96 and then retaken by the grasper at the distal end of the needle, or the point end of the needle projecting from beneath the first suture loop 104 and out of the slot as viewed in FIG. 8. The needle and attached suture material are then pulled from the instrument slot and from beneath the first suture loop 104 causing the first loop to move off of the first end of the rod as shown in FIG. 9. As the needle and first end of the suture are continued to be pulled away from the rod first end by the grasper, the first loop 104 moves down along the length of suture attached to the needle toward the stitch made at the surgical location in the tissue defect 90, forming a first throw of a knot in the suture material securely closing the stitch, as shown in FIG. 10.

The above process is repeated with the needle and attached suture passing through the slot and beneath the second loop 106 of suture formed on the exterior of the rod first end. As the needle and attached suture are pulled out of the slot and from beneath the second loop 106, the second loop is pulled off the rod first end down the length of suture attached to the needle. As the needle and attached suture are continued to be pulled away from the rod first end, the second loop arrives at the stitch formed by the first throw and forms a second throw of the knot at the stitch. If so desired, the procedure is repeated a third time by inserting the needle beneath the third loop 108 of suture and pulling the needle from beneath the loop and from the rod first end to cause the third loop to move off the rod end and down the suture forming a third throw in the knot at the stitch. This procedure may be repeated as many times as there are suture loops formed on the rod first end to form a knot of any desired number of throws. When the desired knot is formed at the stitch in the surgical location, the two lengths of suture extending from the knot are cut and the knot-tying instrument and needle are removed from the surgical location.

It should be appreciated that the surgical instrument of the invention facilitates tying a knot in a length of suture material at a remote surgical location by enabling the positioning of the suture material proximate to the surgical location and by holding the suture material at the surgical location in a manner that enables one or more throws of a knot to be easily formed in the suture material.

Figure 11:
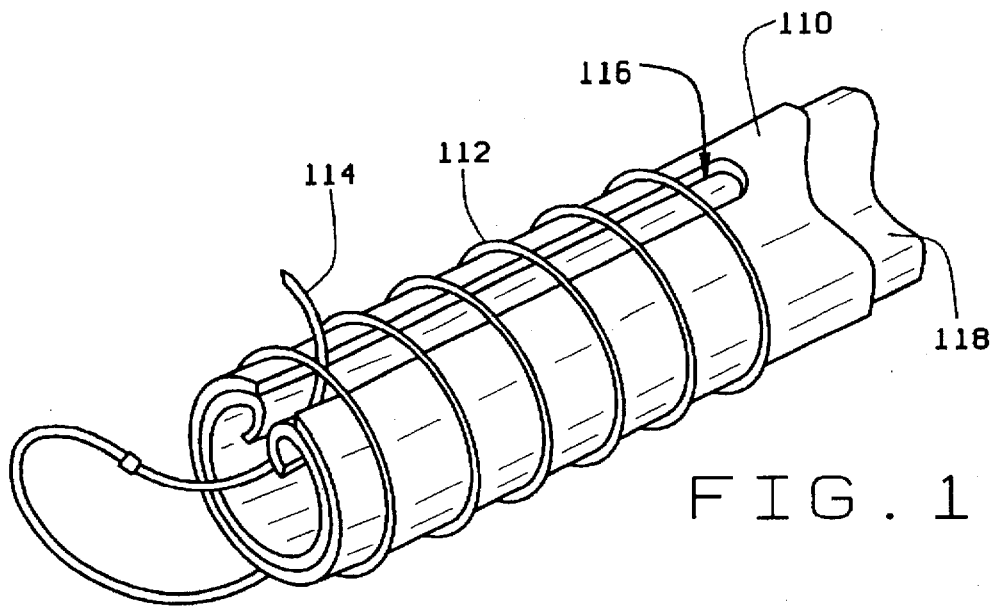
FIG. 11 shows a partial perspective view of a further embodiment of the invention.

FIG. 11 shows a still further embodiment of the rod 110 of the surgical instrument similar to the embodiment shown in FIG. 3. In this embodiment, the rod has substantially the same configuration as the embodiment shown in FIGS. 1 and 4 with the length of suture material 112 and the needle 114 affixed thereto looped over the exterior surface of the rod 110 in substantially the same manner as that described with reference to FIGS. 1 and 4. The rod 110 has a slot 116 formed in its first end in the same manner as the previously described embodiment of FIGS. 1 and 4 and the length of suture material is looped over the slot. Like the FIG. 3 embodiment, in the FIG. 11 embodiment the longitudinal length of the surgical instrument is divided into two sections, with the first section comprising the rod 110 and the second section comprising a tubular handle 118 having a first end inserted through the interior of the rod. As shown in FIG. 11, the rod 110 is detachably secured to the first end of the handle 118 by being slipfit over the end of the handle. The interior diameter of the rod 110 is substantially equal to the exterior diameter of the handle 118 so that the rod 110 may be easily slipfit over the end of the handle 118 and held on the handle end by friction engagement. The rod has a slot 120 that is equal in length to the slot 116 of the rod and is aligned with the rod slot. Like the embodiment of FIG. 3, the longitudinal length of the instrument handle 118 enables it to be used in both deep open incisions or in laparoscopic surgery as in the previously described embodiments. The ability of the rod 110 to be detached from the handle 118 enables the rod to be detached and disposed of after use and replaced on the handle by a like rod. With the configuration of the surgical instrument shown in FIGS. 11 and 12, once the length of suture has been used from one rod 110 of the instrument the used rod may be detached from the handle 118 and replaced with a new rod having a length of suture looped over its exterior surface.

Figure 12:
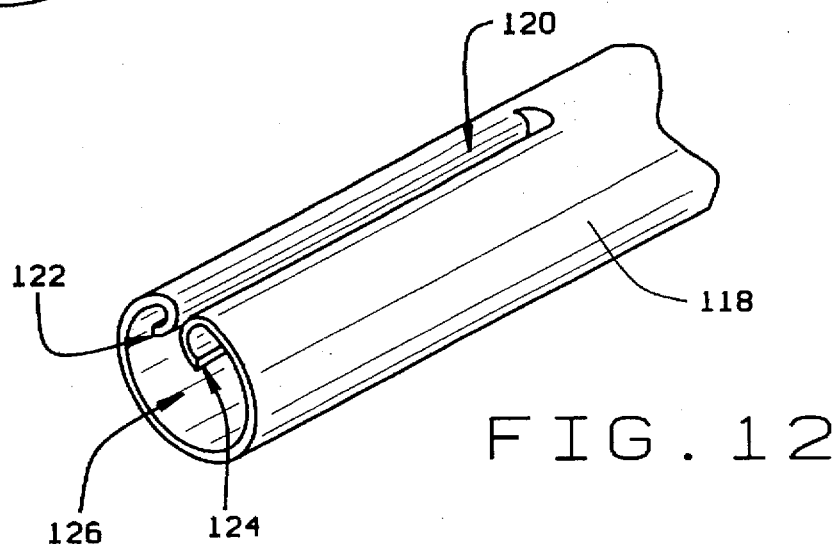
FIG. 12 shows a partial perspective view of a handle used with the embodiment of FIG. 11.

As explained above, the handle slot 120 has a longitudinal length substantially equal to that of the rod slot 116 but is also provided in a specific configuration that enables the handle slot 120 to grip the needle 114 between the opposite lateral edges of the slot. With the handle slot 120 having such an ability, it is no longer necessary to provide a magnetic strip along the slot of the rod 110 to temporarily hold the needle 114 while using the instrument of the invention. As best seen in FIG. 12, the opposite lateral ends 122, 124 of the handle slot 120 are curved underneath and then back toward the interior surface of the handle 118. This gives the handle slot 120 a much narrower width than the slot 116 of the rod 110 enabling it to pinch grip the needle 114 within the slot.

Figure 13:
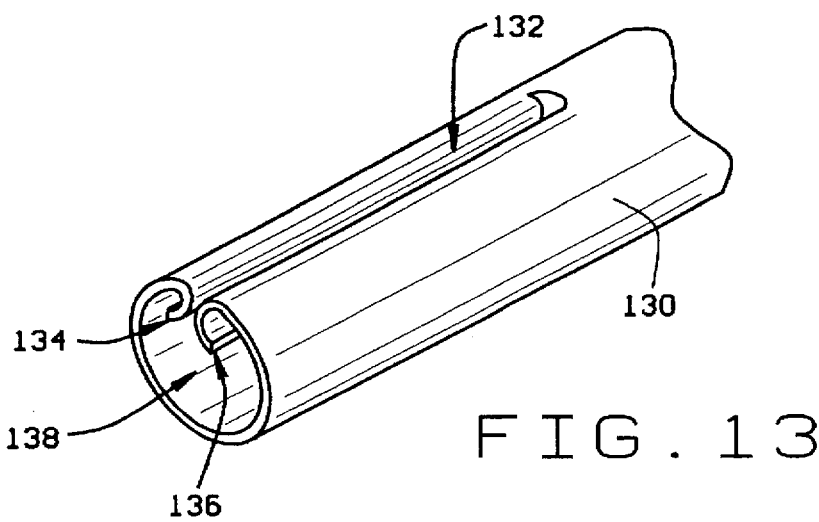
FIG. 13 shows a partial perspective view of a further embodiment of the invention.

A still further embodiment of the rod 130 of the surgical instrument of the invention is shown in FIG. 13. This embodiment of the rod 130 is substantially identical to the first described embodiment of FIGS. 1 and 4 except for the configuration of the rod slot 132. The first end of the rod 130 has the same cylindrical configuration of the first described embodiment of FIGS. 1 and 4 and although not shown, a length of suture material is wrapped over the exterior surface of the rod and the slot 132 with one end of the suture secured to the rod and the opposite end of the suture secured a needle in the same manner as the first described embodiment. The embodiment of FIG. 13 differs from the previously described embodiment of FIGS. 1 and 4 in that the configuration of the slot 132 is substantially identical to that of the just described embodiment of the instrument handle 118 shown in FIGS. 11 and 12.

FIGS. 14–17 show a still further embodiment of the surgical instrument of the invention. Like the previously described embodiments of the invention, the embodiment of FIGS. 14–17 is also comprised of a tubular rod 150 with opposite ends 152, 154 and a length of suture material 156 wrapped around one end. However, in this embodiment the rod is an inner rod 150 of a surgical instrument comprised primarily of a pair of concentric rods. In addition to the inner rod 150, the surgical instrument of FIGS. 14–17 also comprises an outer rod 158, an annular shoulder 162 with a sealing cap 164, a manual handle 166 and a spring 168. As with the previously described embodiments, the component parts of the embodiment shown in FIGS. 14–17 may be constructed of any materials acceptable for use in surgical instruments. Additionally, the dimensions of the component parts of the instrument shown in the drawing figures are chosen to better illustrate the component parts of the invention and are not to scale and should not be interpreted as limiting. The dimensions of the component parts of the embodiment shown in FIGS. 14–17 may be varied to best suit the embodiment of the surgical instrument of the invention shown in these drawing figures to any particular surgical operation.

First referring to the inner rod 150 of the instrument, the inner rod 150 has a longitudinal length with a first, distal end 152 and a second, proximal end 154. The inner rod is provided with a cylindrical exterior surface 172 that extends between the opposite distal and proximal ends. A portion of the rod distal end is formed as a two-pronged fork 174. The space between the prongs of the fork 174 is dimensioned large enough for a single strand of suture material to pass through the space but will prevent a knot in a strand of suture material from passing through the space. This dimensioning of the space between the fork prongs enables the fork to be used in manipulating a knot along a length of suture material. A longitudinal slot 175 is provided in the rod distal end opposite the fork 174. The slot 175 is employed in the same manner as the slots in the ends of the previously described embodiments. The inner rod 150 also has a cylindrical interior bore 176 that extends completely through the rod between its distal and proximal ends. A circular opening 178 extends through the inner rod 150 from the exterior surface 172 to the interior bore 176.

The length of suture material 156 extends from a proximal, free end of the suture along the length of the instrument and is wrapped in a desired pattern of loops on the distal end 152 of the inner rod. From the pattern of loops wrapped on the inner rod, the length of suture material then continues to its distal end, where it may be secured to a needle. The manner in which the length of suture material 156 is wrapped on the surgical instrument in preparation for use of the instrument will be described later in this specification.

The outer rod extends between a first, distal end 182 of the rod to a second, proximal end 184 of the rod. The outer rod 158 also has a cylindrical exterior surface 186 except for external screw threading 188 formed on the exterior surface adjacent the proximal end 184 of the rod. The outer rod 158 also has a cylindrical interior bore 192 extending completely through the rod between its distal and proximal ends. The interior diameter of the bore 192 generally matches the exterior diameter of the inner rod 150 enabling the inner rod 150 to be received in the interior bore 192 of the outer rod 158 for sliding, reciprocating movement therein. The longitudinal length of the outer rod 158 and its interior bore 192 is determined so that the entire longitudinal length of the inner rod 150, except for the fork 174 projecting from its distal end, can be completely received in the outer rod interior bore 192. At the outer rod distal end 182 the annular end face 194 of the rod surrounds the exterior surface of the inner rod 150 in close conformity. This enables the annular end face 194 to slide the loops of suture material 156 wrapped over the exterior surface of the inner rod over the inner rod exterior surface and off the distal end of the inner rod as the inner rod is reciprocated into the interior bore 192 of the outer rod. An elongated opening or slot 196 extends through the outer rod 158 from the exterior surface to the interior bore 192.

The annular shoulder 162 is screw threaded on the proximal end 184 of the outer rod 158. Alternatively, the shoulder could be silver soldered in place on the outer rod. The shoulder also has an interior bore 198 with internal screw threading 202 that is complementary to the external screw threading 188 of the outer rod distal end. An end wall 204 of the shoulder has a small diameter opening 206 extending therethrough communicating with the interior bores of the concentric rods 150, 158. A circular flange 208 surrounds the periphery of the end wall. An elastic sealing cap 164 is fitted over the circular flange 208 and covers over a portion of the end wall opening 206. The sealing cap 164 has a center opening 214 that communicates with the end wall opening 206 but is smaller in diameter and area than the end wall opening 206. At the opposite end of the shoulder 162 an annular groove 216 is formed completely surrounding the exterior surface of the outer rod 158.

The coiled spring 168 is received over the exterior surface of the outer rod 158. The spring has opposite distal 218 and proximal 222 ends and the proximal end of the spring is nested in the annular groove 216 of the shoulder 162.

The handle 166 is mounted on the exterior surface of the outer rod 158 for sliding, reciprocating movement thereon. The peripheral surface 224 of the handle is given a general concave configuration that enables the handle to be gripped easily between adjacent fingers of a surgeon's hand. To facilitate assembly of the handle onto the outer rod 158, the handle is formed in two halves 228, 232 best seen in FIG. 3. The two handle halves are formed with flat mating surfaces 234 with semicircular recesses 236 extending through the middle of the flat mating surfaces. The curvature of the semicircular recesses 236 conforms to the cylindrical exterior surface of the outer rod 158 enabling the two handle halves to come together and easily slide over the exterior surface of the outer rod. A cylindrical pin 238 extends from the semicircular recessed surface 236 of one of the handle halves. The length and diameter of the pin 238 is determined so that it will extend through the elongated slot 196 in the side of the outer rod 158 and into the circular opening 178 in the side of the inner rod 150, thereby connecting the handle half to the inner rod. The flat surface 234 of one of the handle halves 228 has an additional pair of projecting pins 242 thereon. The flat surface of the mating handle half 232 has a pair of holes 244 recessed therein dimensioned to receive the pair of pins 242 of the other handle half in assembling the two handle halves together over the exterior surface of the outer rod. End faces of the handle halves 228, 232 that face the annular shoulder 162 when assembled over the outer rod 158 have semicircular grooves 246, 248 formed therein that together form a circular groove in the handle end face when the two handle halves are assembled together. The circular groove formed is dimensioned to receive the distal end 218 of the coiled spring therein.

The component parts of the surgical instrument of the invention are easily assembled together and disassembled after use to enable sterilization of each of the parts. In assembling the component parts together, the inner rod 150 is first inserted into the interior bore 192 of the outer rod and is positioned so that the hole 178 in the side of the inner rod corresponds to the elongated slot 196 in the side of the outer rod. Next, the two handle halves 228, 232 are assembled over the exterior surface of the outer rod 158 so that the projecting pin 238 on the semicircular recess of the one handle half extends through the elongated slot 196 of the outer rod and into the opening 178 of the inner rod. The length of the projecting pin 238 is determined so that it is sufficiently long to extend through the elongated slot 196 of the outer rod and into the opposed hole 178 of the inner rod without extending into the interior bore of the inner rod. In this manner, the pin 238 does not obstruct the interior bore of the inner rod. In assembling the two handle halves together, the pair of pins 242 on the flat surface of the one handle half 228 are inserted into the pair of holes 244 in the other handle half 232. The handle halves are assembled together so that the semicircular grooves 246, 248 in their end faces face toward the proximal ends of the outer and inner rods.

Next, the distal end 218 of the coiled spring is inserted into the semicircular grooves 246, 248 formed in the handle halves and thereby secures the two handle halves together in their assembled condition around the exterior surface of the outer rod. The annular shoulder 162 is then screw threaded onto the screw threading 188 of the outer rod. As the annular shoulder 162 is screw threaded onto the outer rod, the coiled spring proximal end 222 is inserted into the annular groove 216 of the shoulder. When the annular shoulder 162 is threaded to its furthest extent onto the distal end of the outer rod 158, the coiled spring 168 will be slightly compressed.

When the shoulder 162 is soldered in place on the outer rod the spring is first assembled on the outer rod and compressed. Then the handle halves are assembled on the outer rod and the spring released, holding the handle halves in place.

From the above described assembly of the instrument it should be apparent that the slightly compressed spring 168 will bias the handle 166 away from the annular shoulder 162. By the connection of the handle to the inner rod 150 through the pins 238, the coiled spring 168 will also bias the inner rod 150 to its extended position relative to the outer rod 158 exposing a portion of its exterior surface adjacent the distal end 152 of the inner rod.

In use of the instrument of the invention, the length of suture material 156 having the needle secured at its distal end and a free proximal end is first wrapped in a desired pattern of loops on the inner rod exterior surface 172 projecting from the outer rod distal end 182. The free or proximal end of the length of suture is held at the proximal end of the instrument, or the right hand end as viewed in drawing FIGS. 1 and 2, either by the surgeon's hand or by a clamp on the exterior surface of the outer rod 158 which will be described later. The length of suture material is then extended longitudinally from its proximal end toward the exterior surface 172 of the inner rod distal end projecting from the distal end of the outer rod. On this exposed portion of the inner rod exterior surface, the length of suture material 156 is wrapped in a desired pattern of loops. The pattern of loops can be that described earlier with reference to other embodiments of the invention, or can be any pattern of loops that will produce a knot in the suture material when the suture loops are displaced off the distal end 152 of the inner rod and the needle at the distal end of the suture material is inserted through the center of the pattern of loops and is pulled tight. For example, the pattern of suture loops wrapped on the inner rod distal end can be that of a surgeon's knot, a Roeder's knot, a modified Roeder's knot, or any other pattern of suture loops that will form a knot that will slide over the portion of the length of suture connected to the needle when the needle is inserted through the centers of the loops as the loops are pushed off of the inner rod distal end onto the needle and attached portion of suture. After forming the desired pattern of suture loops on the inner rod distal end 152, the length of suture material then extends to the needle at its distal end. This excess length of suture material is needed to enable manipulation of the needle by the surgeon in making a stitch through body tissue with the needle. This excess length of suture material can be wrapped spirally on the inner rod distal end adjacent the pattern of loops formed on the inner rod in order to take up the slack in the suture material. The needle may then be inserted into the interior bore of the inner rod 150 and held by a surgical grasper (not shown) adjacent the inner rod distal end as the surgical instrument, with the grasper in its interior, is inserted through a trocar to a desired position in the body cavity.

With the instrument inserted into the body cavity so that the distal ends of the inner 150 and outer 158 rods are positioned proximate to the site in which a stitch is to be made, the grasper inserted through the interiors of the inner and outer rods may then be used to manipulate the needle at the end of the length of suture out of the interior bore of the inner rod 150. The same grasper inserted through the interiors of the inner and outer rods may be used to make the stitch in the body tissue. The grasper then regrips the needle at the opposite side of the stitch and returns the needle to the interior bore of the inner rod 150, pulling the length of suture wrapped spirally on the distal end of the inner rod from the rod end and through the stitch and back into the interior bore of the inner rod 150. As the needle and attached length of suture are pulled back into the interior bore of the inner rod 150, the length of suture is threaded through the pattern of loops formed on the exterior surface 172 of the inner rod distal end. With the length of suture passed through the stitch being pulled taut and with the distal end of the inner rod 150 positioned proximate to the site of the stitch, the handle 166 is then manually retracted toward the annular shoulder 162 against the bias of the spring 168 causing the annular end face 194 of the outer rod to push the pattern of loops formed in the length of suture off of the inner rod exterior surface 172 and over the length of suture connected to the needle. With the pattern of loops pushed off the distal end of the inner rod 150, the loops are snugged up about the suture and slid toward the stitch. The fork 174 formed at the distal end of the inner rod may be used to manipulate the pattern of loops toward the site of the stitch in the body tissue. The portion of suture material connected to the needle is further tightened by retracting the grasper through the interior of the inner rod 150 toward the proximal end of the instrument. The proximal end of the suture material held by the surgeon's hand or by the clamp at the proximal end of the instrument is also tightened, causing the pattern of loops formed in the suture material to constrict into a knot formed in the suture material at the site of the stitch. In the case of a surgeon's knot, each throw is slid to the site of the stitch and tightened before introducing another throw to the knot. With the knot tightened at the site of the stitch, the two portions of suture material leading from the stitch may then be cut free at the knot and removed from the site of the stitch formed. The instrument may then be reloaded with a length of suture wrapped in the desired pattern of loops on the inner rod distal end to form the next stitch in the body tissue.

To assist in reloading suture material wrapped in a desired pattern of loops onto the distal end of the inner rod 150, the surgical instrument of the invention also includes a cartridge 252 that is partially shown in FIGS. 14 and 17. The cartridge is basically a cylindrical tube having an exterior surface with a cylindrical configuration and exterior diameter substantially identical to that of the inner rod 150. The cartridge 252 has a length of suture material wrapped in the desired pattern of loops over its exterior surface. The length of suture material 254 is wrapped around the exterior diameter in reverse order so that it can be slipped off the exterior surface of the cartridge 252 and onto the exterior surface 172 of the inner rod adjacent its distal end 152 and be in the proper orientation for use. In this manner the cartridge 252 enables the surgeon to quickly reload the instrument with a length of suture wrapped in the desired pattern of loops on the inner rod distal end 152 in preparation for making the next stitch with the instrument.

In order to facilitate transfer of the loops from the cartridge 252 to the exterior surface 172 of the inner rod, a pair of slidable tongs 260 may be provided. The tongs 260 are in the form of a cylinder having two tines extending along the cartridge 252. Each tine 262 has a T-shaped head 264 which may be used to grip an individual set of loops. Once the loops are gripped, the tongs 260 may be slid along the exterior surface of the cartridge 252 toward the inner rod to thereby transfer the loops from the cartridge to the distal end 152 of the inner rod. The tongs are made of a suitably resilient material such that when the tines are released, the T-shaped heads return to their original position and the tongs may be retracted onto the cartridge. In the preferred embodiment, the inner diameter of the tongs is large enough to permit loops of suture wound about the exterior surface of the cartridge to pass through the interior of the tongs. Thus, several sets of loops may be preloaded onto the cartridge and the tongs may be used to individually dispense one set of loops at a time without disturbing the other preloaded sets. Alternatively, some means of spring ejection may be employed to facilitate loading the loops onto the distal end 152 of the inner rod.

An alternative to the cartridge 252 described above is a detachable segment 272 of the inner rod distal end. The detachable segment is represented by the dashed lines 274 shown in FIG. 14. The detachable segment 272 of the inner rod may be screw threaded to the distal end of the rod to enable its quick replacement. The detachable segment 272 has the length of suture wrapped in the desired pattern of loops thereon when it is attached to the distal end of the inner rod 150. After the pattern of loops of suture material have been dispensed from the segment by operation of the instrument as described above, the instrument can be quickly reloaded with another length of suture wrapped in the desired pattern of loops by removing the spent segment 272 from the end of the inner rod and replacing it with a like segment having the desired pattern of loops of suture material wrapped thereon. With the instrument quickly reloaded in this manner, it is then again ready for use in forming a stitch in body tissue at a remote location in the same manner as described above.

Figure 16:
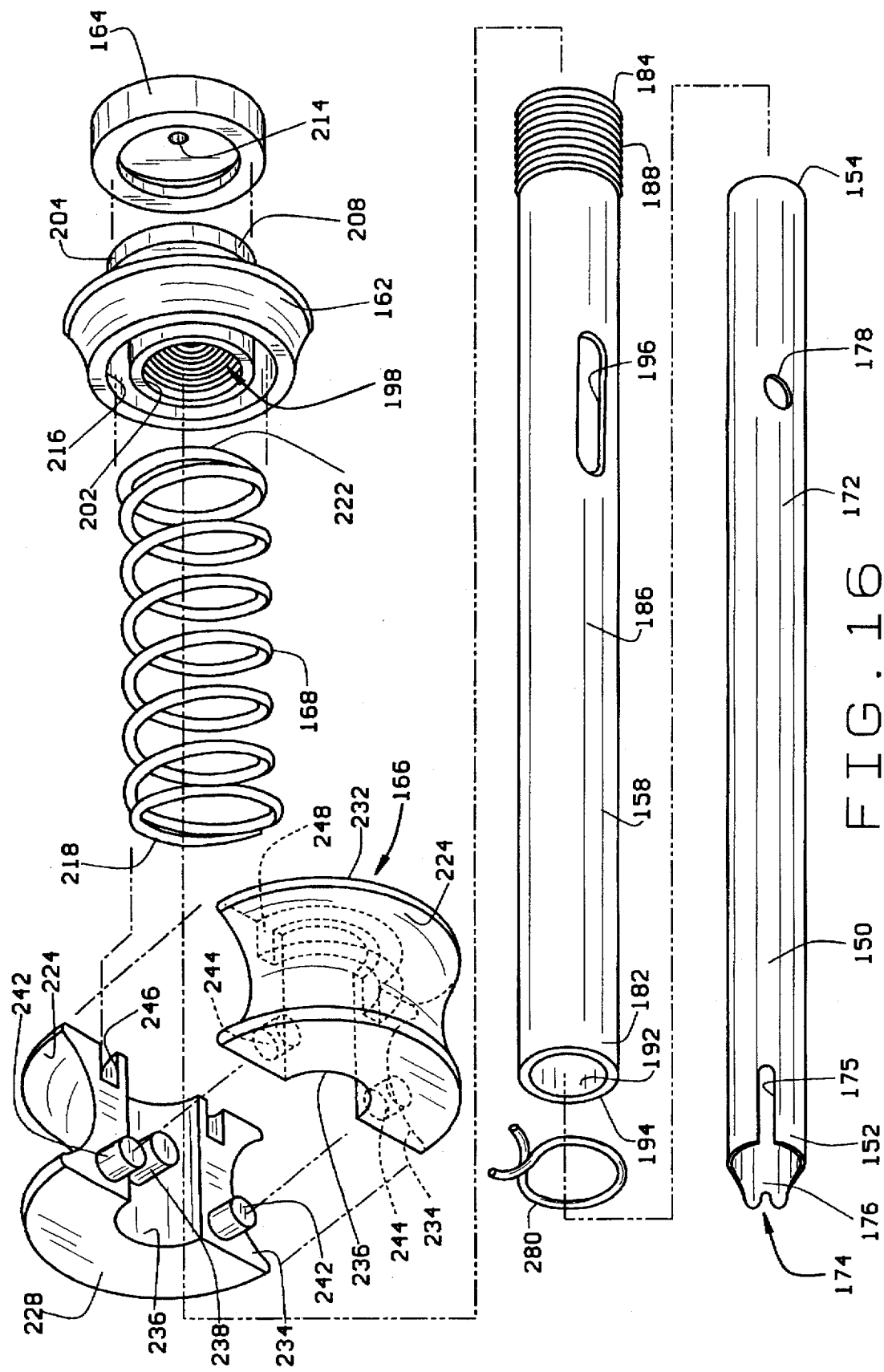
FIG. 16 shows an instrument of FIG. 14 disassembled.

A typical wire hose clamp 280 may be clamped over the cylindrical exterior surface 186 of the outer rod 158 as shown in FIGS. 14 and 16. Wrapping the suture around the horns of the hose clamp two or three times grips the free end of the suture sufficiently to prevent it from being separated from the hose clamp. Thus, the free end of the suture may be attached to the instrument until ready for manipulation. Alternate clamps and other attachment means are also within the scope of this invention.

Figure 18:
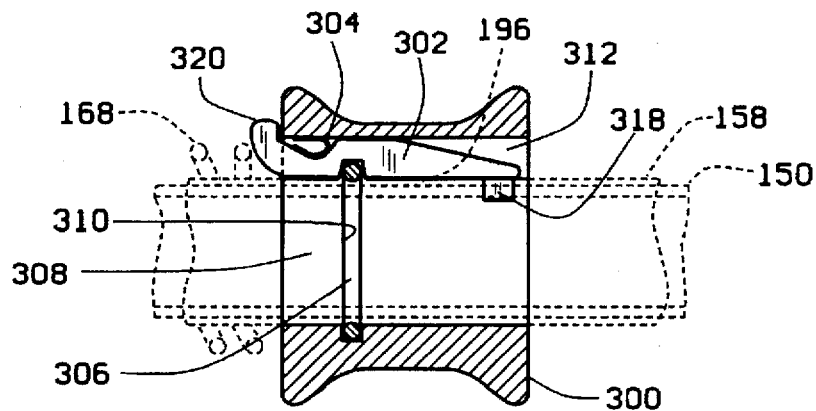
FIGS. 18–21 show variant embodiments of the instrument handle.
Figure 19:
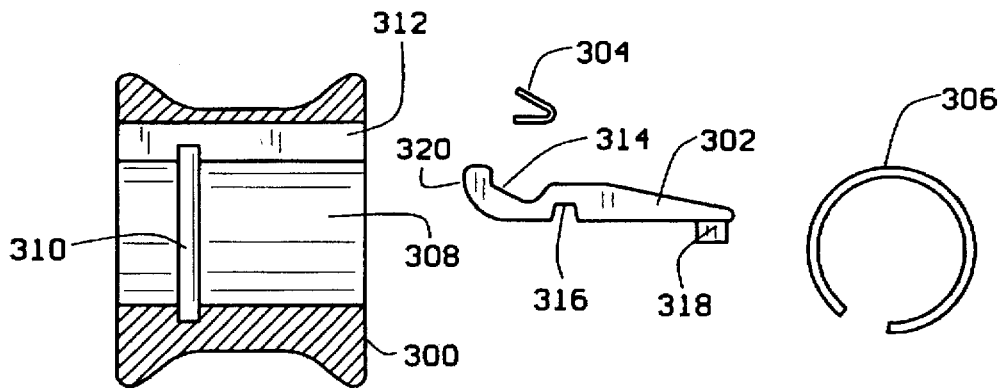

FIGS. 18–21 show variant embodiments of the handle of the surgical instrument of the invention. FIGS. 18 and 19 disclose a first embodiment of these handle variants with the handle shown assembled to the concentric tubular rods in FIG. 18 and shown disassembled into its component parts in FIG. 19.

The handle embodiment of FIGS. 18 and 19 is comprised of a cylindrical handle member 300, a locking lever 302, a leaf spring 304 and a circular spring 306.

The handle member 300 is very similar to the handle of the previously described embodiment of the instrument except that it is provided as a single cylindrical member instead of two half members. The exterior configuration of the handle member is substantially identical to that of the handle of the previously described embodiment. A cylindrical bore 310 extends through the center of the handle member 300. The bore has an interior diameter that is matched to the exterior diameter of the outer rod so that the handle member 300 may be mounted for sliding reciprocating movement over the exterior of the concentric rods as is shown in FIG. 18 where the concentric rods are represented in phantom lines. An annular groove 310 extends completely around the interior bore 308 of the handle member. An axial slot 312 is formed in the interior bore 308 extending the axial length of the bore.

The locking lever 302 has a width dimension determined to enable the locking lever to be inserted into the axial slot 312 of the handle member in the position shown in FIG. 18. A recess 314 is provided in the top of the locking lever 302 and the leaf spring 304 is received in the recess as the locking lever 302 is positioned in the axial slot 312. To hold the locking lever and leaf spring in their relative positions in the slot 312 shown in FIG. 18, a notch 316 is provided in the bottom of the locking lever 302 opposite the leaf spring recess 314. The circular spring 306 is compressed and inserted into the handle member interior bore 308 where it is positioned in the annular groove 310 and the lever notch 316. The resiliency of the circular spring 306 holds the locking lever 302 in the axial slot 312 of the handle member.

With the component parts of the handle assembled together and prior to their positioning on the exterior of the outer rod of the instrument, the leaf spring 304 pivots the locking lever 302 in the axial slot 312 and about the circular spring 306 so that a pin 318 of the lever 302 is retracted into the axial slot 312 of the handle member. With the pin 318 in the axial slot, the assembled component parts of the handle can be easily slipped over the exterior surface of the outer rod of the instrument. The end 320 of the locking lever that projects from the handle member axial slot 312 is moved radially outwardly relative to the handle member 300 to cause the lever pin 318 to engage through the elongated slot 196 of the outer rod member and into the circular opening 178 of the inner rod member, thereby connecting the handle member 300 to the inner rod member. The coil spring 168 of the instrument engages against the locking lever end 320 and maintains the locking lever in the position shown in FIG. 18 with the lever pin 318 inserted through the slot 196 of the outer rod member and into the opening 178 of the inner rod member.

Figures 20, 21:
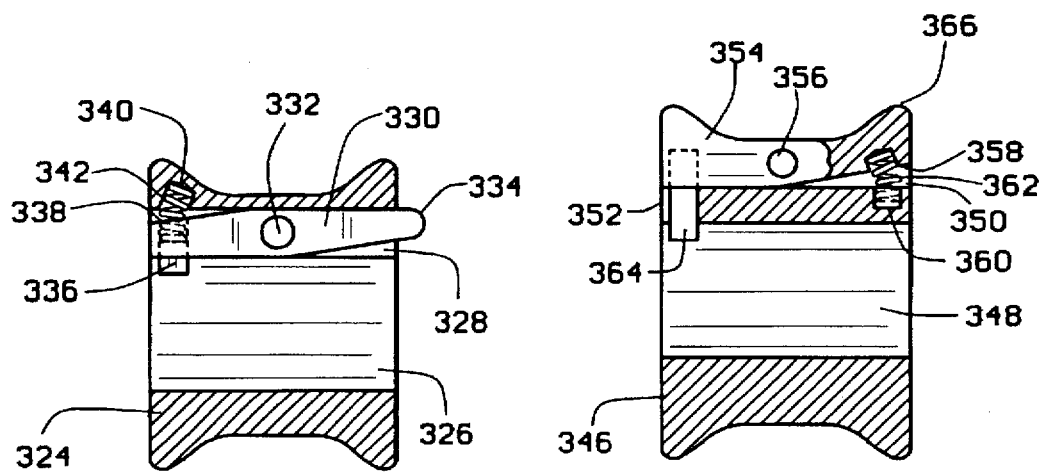

A further embodiment of the handle member 324 is shown in FIG. 20. This embodiment is similar to the embodiment of FIGS. 18 and 19 in that it is basically comprised of a cylindrical one piece handle member 324 with a cylindrical interior bore 326 extending through its center and an axial slot 328 extending along one side of the interior bore. A locking lever 330 is positioned in the axial slot 328 and a pivot pin 332 is inserted into the handle member and the locking lever to mount the locking lever in the axial slot 328 for pivoting movement of the lever about the pin. An end 334 of the lever projects from the handle axial slot 328 and a lever pin 336 projects from the opposite end of the lever. The lever pin 336 projects through the elongated slot 196 of the outer rod and into the circular opening 178 of the inner rod (not shown in FIG. 20) in connecting the handle to the inner rod. This connection is much the same as the handle embodiment of FIGS. 18 and 19. A spring hole 338 is formed in the top of the lever 330 opposite the lever pin 336 and a corresponding spring hole 340 is formed in the handle member 324 at the top of the axial slot 328. A small coil spring 342 is inserted into the lever hole 338 and the handle hole 340 biasing the locking lever 330 to the position shown in FIG. 20 where the lever pin 336 extends through the outer rod slot 196 and into the inner rod circular opening 178 connecting the handle member 324 to the inner rod.

The handle embodiment of FIG. 20 is assembled onto the outer rod of the instrument by depressing the projecting end 334 of the lever thus raising the lever pin 336 into the axial slot 328. The handle member 324 is then slipped over the exterior surface of the outer rod until it is properly positioned over the outer rod slot 196 and the inner rod circular opening 178. The end 334 of the locking lever is then released, causing the coil spring 342 to push downward on the locking lever and thereby causing the lever pin 336 to be inserted through the outer rod slot 196 and into the inner rod circular opening 178 connecting the handle member to the inner rod.

A still further embodiment of the handle is shown in FIG. 21. The FIG. 21 embodiment is also comprised of a single piece, cylindrical handle member 346 as were the previous embodiments of FIGS. 18–20. The handle member 346 has a cylindrical interior bore 348 extending through its center. However, unlike the previously described embodiments of the handle member, the FIG. 21 embodiment has an axial slot 350 extending into the handle member from its exterior surface. A notch 352 also extends from the axial slot 350 through to the handle member interior bore 348.

A locking lever 354 is positioned in the axial slot 350 and held in place by a pivot pin 356. As seen in the drawing figure, a portion of the bottom surface of the locking lever 354 is cut away so that the locking lever bottom surface tapers away from the bottom of the handle member axial slot 350. This enables the locking lever to pivot in the axial slot about the pivot pin 356. A spring hole 358 is formed in the tapered bottom surface of the locking lever 354 and a second spring hole 360 is formed in the bottom of the handle member axial slot 350 opposite the locking lever spring hole. A small coil spring 362 is assembled into the spring holes of the locking lever and the handle member. The coil spring biases the locking member to its position relative to the handle member shown in FIG. 21. The opposite end of the locking lever 354 has a lever pin 364 extending downwardly therefrom. The lever pin 364 extends through the notch 352 of the handle member and into the handle member interior bore 348 where it extends through the elongated slot 196 of the outer rod member and into the circular opening 178 of the inner rod member, thereby connecting the handle member 346 to the inner rod.

In mounting the embodiment of the handle shown in FIG. 21 on the exterior surface of the instrument outer rod, the end of the locking lever 366 is first depressed against the bias of the coil spring 362 causing the lever to pivot about the pivot pin 356 and retracting the lever pin 364 from the interior bore 348 and into the notch 352. The handle member 346 is then slipped over the exterior surface of the instrument outer rod until it is positioned over the outer rod elongated slot 196 and the inner rod circular opening 178. The lever end 366 is then released causing the coil spring 362 to pivot the locking lever about the pivot pin 356 and causing the lever pin 364 to be inserted through the elongated slot 196 of the outer rod and into the circular opening 178 of the inner rod, thereby connecting the handle member to the inner rod.

FIGS. 22-25 show a still further embodiment of the surgical instrument of the invention. In this embodiment, the instrument is specifically designed to facilitate tying ligatures in a length of suture material. Like previously described embodiments, this embodiment is also comprised of a tubular inner rod 400 with a distal end 402 and a proximal end (not shown). The inner rod has a hollow interior bore extending through the rod between its opposite ends. The rod interior bore is divided into a first interior bore 404 and a second interior bore 406 by an interior wall 408 that extends axially through the interior of the inner rod dividing it into the two separate interior bores. As can be seen in the cross-section of FIG. 23, the second interior bore 406 has a substantially larger cross-sectional area than the first interior bore 404. The larger cross-sectional area of the second interior bore 406 is sufficient to enable insertion of a conventional surgical instrument, for example a surgical grasper, through the second interior bore of the inner rod as in previously described embodiments of the inner rod. Also shown in FIG. 23, the interior wall 408 has a flat surface that faces the first interior bore 404.

A resilient and flexible filament 410 passes through the first interior bore 404 of the inner rod. The filament has opposite proximal 412 and distal 414 ends. The filament is received in the interior bore 404 for sliding reciprocating movement of the filament through the bore. As shown in FIG. 23, the filament has a generally rectangular cross-section that occupies much of the first interior bore and has a flat bottom surface that opposes the flat surface of the interior wall 408 facing the interior bore 404 as viewed in FIG. 23. These mutually opposed flat surfaces prevent the filament from rotating in the first interior bore and thereby maintain a position of the filament distal end 414 in front of the inner rod distal end 402. As shown in FIG. 22, the proximal end 412 of the filament has a preformed curvature that forms a handle that facilitates grasping of the proximal end by the surgeon to pull the filament through the interior bore 404, or push the filament into the interior bore at the proximal end of the instrument. A portion of the filament adjacent its distal end 414 is also formed in a curved configuration. The very tip of the filament distal end has a small slot 416 formed therein. The slot is dimensioned to receive and releasably hold a length of suture 418 at the distal tip of the filament. From the slot 416, the suture 418 extends toward the instrument and is wrapped in a knot 420 on the distal end of the inner rod 400.

The inner rod 400 is received for reciprocating movement in the interior bore of an outer rod 422 as in previously described embodiments. The outer rod 422 is identical to the outer rod of previously described embodiments and comprises a distal end 424 and an opposite proximal end 426. The annular shoulder 428 and sealing cap 430 are provided on the proximal end of the outer rod. The manual handle 432 is mounted for limited reciprocating sliding movement on the exterior of the outer rod 422, and the coil spring 434 is mounted over the exterior of the outer rod between the handle 432 and the annular shoulder 428. A clamp 436 is also provided on the exterior of the outer rod for securing the free end of the suture 418 thereto.

As with the drawings of the previously described embodiments, the dimensions of the component parts of the instrument shown in FIGS. 22-25 are chosen to better illustrate the component parts of the invention and are not to scale and should not be interpreted as limiting. The dimensions of the component parts shown in the drawing figures may be varied to best suit the embodiment of the surgical instrument of the invention shown to any particular surgical operation.

The operation of the instrument shown in FIGS. 22-25 is substantially identical to that of previously described embodiments when ejecting the suture knot 420 off of the distal end 402 of the inner rod 400. In use of this instrument, prior to its insertion through a canula to position the inner rod distal end 402 adjacent tissue to be ligated, the filament proximal end 412 is gripped by the surgeon and pulled so that the filament passes through the first interior bore 404 of the inner rod. The filament distal end 414 is drawn into the first interior bore 404 at the distal end of the inner rod 400. Pulling the filament distal end into the bore straightens its curved configuration. The filament also pulls a portion of the suture 418 secured in the filament slot 416 into a portion of the inner rod first interior bore 404 adjacent the distal end 402 of the rod. This eliminates any loose suture hanging from the distal end of the instrument.

Next, the inner rod distal end 402 is passed through the canula and is positioned adjacent the tissue to be ligated. When in its desired position, the surgeon manipulates the filament proximal end 412 pushing the filament into the first interior bore 404 of the inner rod 400 at its proximal end. This causes the filament distal end 414 to extend from the first interior bore 404 at the inner rod distal end 402. As the distal end of the filament is extended from the inner rod interior bore, it returns to its curved configuration shown in FIG. 22. The resiliency of the filament distal end that causes it to return to its curved configuration is also used to pass the free end of the suture 418 around one side and then behind the tissue to be ligated by the suture. With the length of suture passed around and behind the tissue to be ligated by the curved distal end of the filament, a conventional surgical grasper can then be inserted through the inner rod second bore 406 to grasp the end of the suture held by the slot 416 at the filament distal end 414. Pulling the length of suture from the slot releases the suture. The free end of the suture held by the grasper is then pulled into the interior bore of the inner rod 400 at the inner rod distal end 402. Movement of the inner rod distal end 402 toward the outer rod distal end 424 causes the outer rod distal end to push the suture knot 420 off the inner rod distal end 402 and onto the length of suture drawn into the inner rod interior bore by the grasper. The knot pushing slot at the tip of the inner rod distal end 402 may then be used to move the knot along the length of suture pulled into the interior bore of the inner rod by the grasper, thereby moving the knot toward the tissue to be ligated. When the knot is positioned adjacent the tissue, the two free ends of the suture are then pulled tight to tighten the knot around the tissue and complete the ligature. The free ends of the suture may then be cut and removed from the surgical location through the canula with the instrument. Alternatively, as described with reference to previous embodiments, several suture knots may be pre-tied on the inner rod distal end 402. After passing one knot off onto the free end of the suture drawn into the inner rod interior bore, the manual handle 432 may then again be manipulated to cause a second knot to be ejected from the inner rod distal end and onto the suture, thereby forming a knot with two throws around the tissue being ligated.

FIGS. 26–30 show a further embodiment of the ligating instrument shown in FIGS. 22–25. Although this embodiment of the ligating instrument shown in FIGS. 26–30 includes the resilient filament 410, it should be understood that the embodiment of the instrument shown in FIGS. 26–30 may be employed without the filament 410.

The embodiment of the instrument shown in FIGS. 26–30 is identical to the previously described embodiment of FIGS. 22–25 except for the constructions of the distal ends of the inner rod 440 and outer rod 442. All of the remaining component parts of the instrument shown in FIGS. 22–25 remain the same in the embodiment shown in FIGS. 26–30. Additionally, the operation of the instrument embodiment shown in FIGS. 26–30 is substantially the same as that of FIGS. 22–25. Therefore, only the details of the distal ends of the inner rod 440 and outer rod 442 and their manner of operation will be described.

Figure 26:
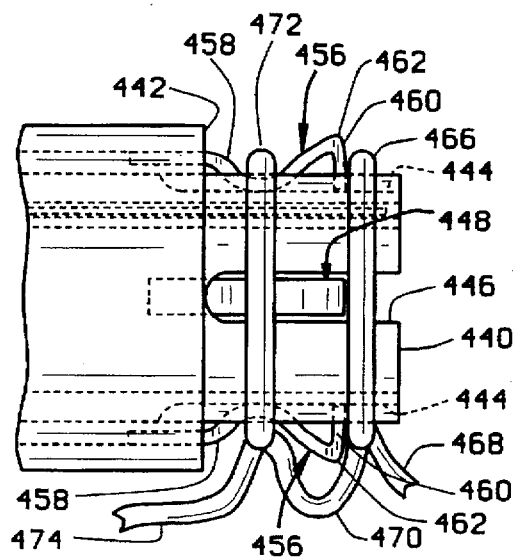
FIGS. 26–30 show a variant embodiment of knot knot tying instrument that comprises suture knot ejecting prongs.
Figure 28:
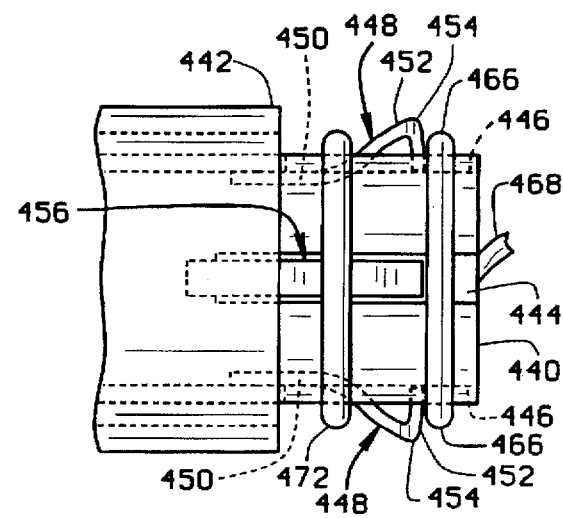
Figure 27:
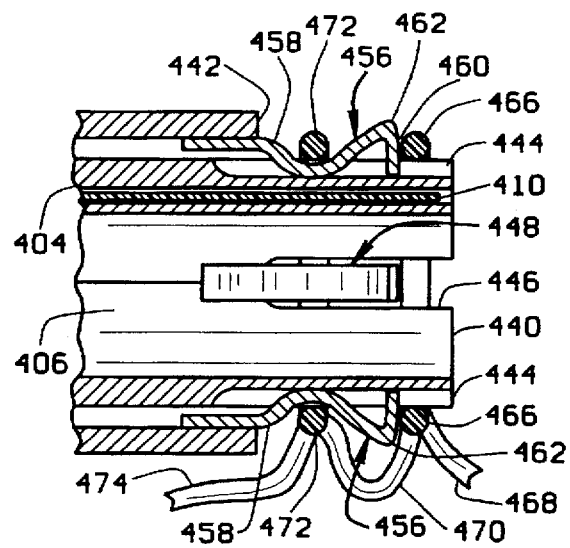
Figure 29:
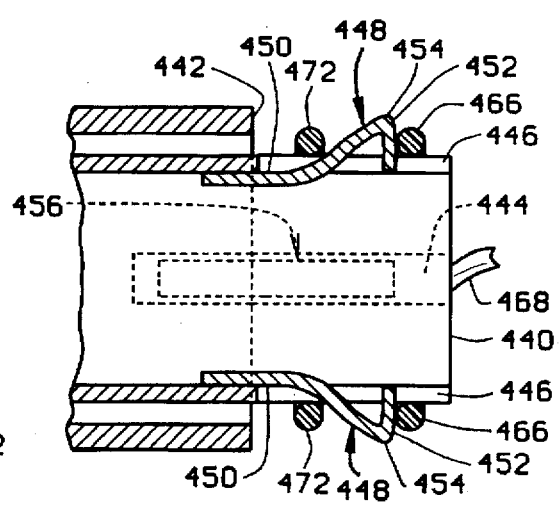
Figure 30:
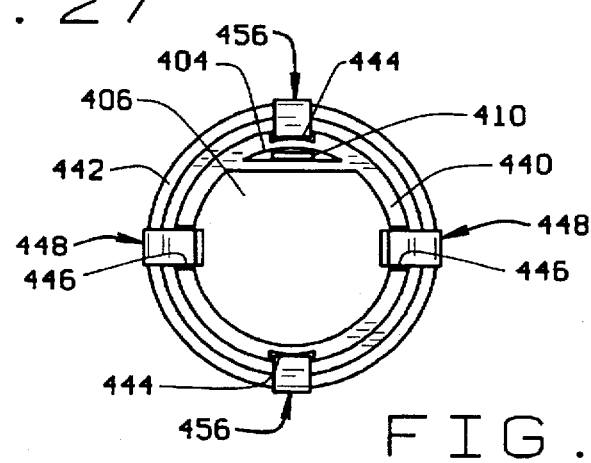

FIG. 27 is a cross-sectional view of the inner rod distal end 440 and outer rod distal end 442 shown in FIG. 26. FIG. 29 is a cross-sectional view of the inner rod distal end 440 and outer rod distal end 442 shown in FIG. 28. The views of the inner and outer rod distal ends shown in FIGS. 28 and 29 are rotated 90° from the orientations of the inner rod distal end and outer rod distal end shown in FIGS. 26 and 27. The schematic representations of the rod distal ends shown in FIGS. 26–30 are not to scale and should not be interpreted as limiting. The dimensions of the component parts of the embodiment of the invention shown in these drawing figures have been enlarged to simplify the description of the component parts. As with previously described embodiments, the dimensions of the component parts of the invention embodiment shown in FIGS. 26–30 may be varied to best suit the embodiment of the surgical instrument to any particular surgical operation.

The inner rod distal end 440 is provided with a pair of axial grooves 444 formed in the exterior surface of the rod. As best seen in FIGS. 27 and 28, the axial grooves 440 are recessed about half way into the side wall of the inner rod 440 from its exterior surface, and extend in an axial direction along the distal end of the rod. The two grooves 444 are positioned on diametrically opposite sides of the inner rod distal end. As shown in FIGS. 26 and 27, one of the pair of grooves 444 is positioned adjacent the first interior bore 404 and the resilient filament 410 passing through the inner rod 400.

Rotated 90° from the pair of grooves 444 on the distal end of the inner rod 440 are a pair of axial slots 446. As best seen in FIGS. 26 and 29, the axial slots 446 pass completely through the side wall of the inner rod distal end 440 and extend axially along the distal end of the rod. The pair of slots 446 are positioned diametrically opposite each other on the inner rod distal end 440.

A first pair of resilient prongs 448 are secured to the interior surface of the inner rod 440 and extend axially toward the inner rod distal end. The prongs are secured to the inner surface of the inner rod by welding or any other equivalent method. From the inner rod inner surface, the first pair of prongs 448 extend along first sections of each of the prongs 450 that are substantially straight. The prongs then extend through second sections that bend radially outwardly through the pair of slots 446 to bends 454 formed in the pair of prongs radially outside the pair of slots 446. From the bends 454, the prongs extend radially inwardly to their distal ends positioned in the slots 446. The first pair of prongs 448 are resilient so that they may bend inwardly through the slots 446 into the second interior bore 406 of the inner rod 400 and return to their configurations extending radially outside the slots as shown in FIG. 29.

A second pair of prongs 456 extends from the distal end of the outer rod 442. Each of the second pair of prongs are secured to the interior surface of the outer rod at its distal end by welding or other equivalent methods. The second prongs extend axially from the outer rod distal end 442 along first sections 458 of the prongs that dip into the pair of grooves 444 of the inner rod distal end 440. From these first sections of the second prongs, the second prongs then extend through second sections of the prongs 460 that extend to bends 462 formed in the prongs spaced radially outside the inner rod grooves 444. From the bends 462, the second prongs then extend radially inwardly to their distal ends positioned in the inner rod grooves 444. Like the first pair of prongs, the second prongs 456 are resilient.

Shown schematically in FIGS. 26–29, a first suture knot 466 is wrapped around the distal end of the inner rod 440. The free end of the suture 468 extends from this first knot 466 to the free end of the suture held at the distal end of the filament 410, and/or to a needle (not shown) secured to the free end of the suture. At the opposite end of the knot 466 toward the proximal end of the instrument, a length of suture 470 extends to a second suture knot 472 wrapped around the inner rod distal end 440 and the first sections 458 of the second prongs 456. From this second knot 472, the free end of the suture adjacent the proximal end of the instrument extends along the length of the instrument and is either held securely by the surgeon or attached to the clamp on the instrument as in previously described embodiments. The first and second suture knots 466, 472 wrapped on the inner rod distal end 440 are only schematically represented in the drawing figures and may be any type of slip knot known now or developed in the future. The operation of the embodiment of the invention shown in these drawing figures is suited to work equally well with any type of slip knot. One length of suture may be employed having several knots wrapped on the inner rod from the one length of suture. Alternatively, several separate lengths of suture may be employed, each wrapped in a separate knot on the inner rod distal end.

The embodiment of the invention shown in FIGS. 26–30 is specifically designed to first eject the first suture knot 466 from the distal end of the inner rod 440 while simultaneously moving the second suture knot 472 axially along the inner rod distal end 440 to the position held by the first suture knot 466 shown in the drawing figures. Thus, while the first suture knot 466 is ejected from the instrument, the second suture knot 472 is moved from its ready position shown in the drawing figures to the position held by the first suture knot 466 shown in the drawing figures where it will be ejected on the next manipulation of the inner rod 440 relative to the outer rod 442.

In use of the embodiment of the instrument shown in FIGS. 26-30, the free end of the suture 468 is first used in placing a stitch or is wrapped around a tissue to be ligated in the same manner as described earlier with reference to previous embodiments. The free end of the suture 468 is then returned to the interior bore of the inner rod 440 by being grasped by a surgical grasper and pulled into the interior bore. The length of suture pulled into the inner rod interior bore is then ready to have a first throw of a knot positioned thereon to tie off the stitch or ligate the tissue. On manual manipulation of the instrument handle as in other embodiments, the inner rod distal end 440 moves leftwardly relative to the outer rod distal end 442 as shown in the drawing figures. As the inner rod moves to the left, the pair of second prongs 456 slide through the opposed grooves 444 of the inner rod pushing the first suture knot 466 before them. As the second pair of prongs 456 push the first suture knot 466 off the inner rod distal end 440, the first suture knot 466 passes onto the length of suture pulled into the interior bore of the inner rod 440. The first suture knot 466 may then be moved down the length of suture to the stitch or tissue being ligated and pulled tight by pulling on the opposite ends of the suture leading from the knot.

Simultaneously with the relative movement of the second pair of prongs 456 through the mutually opposed grooves 444 of the inner rod distal end 440, the first pair of prongs 448 move leftwardly relative to the outer rod distal end 442. As the first pair of prongs 448 move leftwardly, they pass beneath the second suture knot 472 wrapped around the second prong first sections 458. The resiliency of the first pair of prongs 448 allows them to flex inwardly into their associated slots as they pass beneath the second suture knot 472 formed around the second prong first sections 458. As the second prongs 456 elect the first suture knot 466 off the inner rod distal end 440, the bends 454 of the first prong second sections 452 pass beneath the second suture knot 472 and the resiliency of the first prongs causes the second sections of the these prongs to move radially outwardly through their associated slots 466 to position the first prong second sections on the proximal side, or left-hand side as viewed in the drawing figures, of the second suture knots 472. As the inner rod distal end 440 then moves to its at rest position by the bias of the instrument spring, the inner rod distal end 440 moves to the right relative to the outer rod distal end 442 and the first prong second sections 452 push the second suture knot 472 to the right. The first prong second sections 452 push the second suture knot 472 over the second prong bends 462 and position the second suture knot 472 on the proximal or right-hand side of the second prong bends 460 where the second knot is positioned to be next ejected by the second prongs when the instrument handle is again manipulated.

Although the invention is shown with two suture knots schematically represented on the distal end of the inner rod 440, it should be appreciated that the second prongs 456 on the outer rod distal end can be modified to accommodate a third or any number of subsequent knots on the first sections of the second prongs. On manipulation of the instrument handle and reciprocation of the inner rod relative to the outer rod, as one knot is ejected from the instrument by the pair of second prongs, the next subsequent knot in the series is engaged by the first pair of prongs and moved over the second pair of prongs to a position where it is next ejected from the instrument by the second pair of prongs.

FIG. 31 shows a magazine that may be employed with the instrument of FIGS. 26-30 to load a pair of pre-tied suture knots onto the inner rod distal end of the instrument. The magazine 480 is comprised of a cylindrical rod 482 having a reciprocating sleeve 484 mounted thereon. The rod distal end 486 is necked down and has an exterior diameter dimensioned to be received in the interior bore of the inner rod at its distal end 440. An intermediate portion of the rod 488 has a larger diameter than the rod distal end. On this portion of the rod are pre-tied suture knots 490. In the embodiment shown, only two knots are schematically represented on the rod. It should be understood that in variant embodiments of the instrument shown in FIGS. 26-30 that accommodate more than two knots, the magazine would likewise be modified to accommodate a corresponding number of suture knots. The proximal end 492 of the rod is also necked down and has a smaller diameter than the intermediate portion 488 of the rod. A coil spring 494 is positioned on the rod proximal end 492. A circular cap 496 is provided at the end of the rod proximal end 492.

The sleeve has a proximal end wall 498 with an opening 500 therethrough dimension to surround the rod proximal end 492. The sleeve and wall 498 engages the coil spring 494 and compresses the spring between the end wall and the rod intermediate portion 488 as the sleeve is moved leftwardly relative to the rod as viewed in FIG. 31. The spring biases the sleeve rightwardly to its at rest position where the end wall 498 abuts the rod cap 496 as shown in FIG. 31.

At the left-hand end of the sleeve 484 as shown in the drawing, a pair of diametrically opposed prongs 502 project from the sleeve. As seen in the drawing, the prongs 502 are spaced radially outwardly from the exterior surface of the sleeve intermediate portion 488. At the distal ends of the prongs are a pair of fingers 504 connected by living hinges 506 to the prongs. The fingers 504 project inwardly toward the rod intermediate portion 588 in their at rest positions, and can be resiliently extended radially outwardly to positions where they extend substantially parallel with their associated prongs 502.

In use of the magazine, the rod distal end 486 is inserted into the interior bore of the inner rod distal end. The sleeve 484 is then caused to reciprocate to the left over the rod causing the fingers 504 to push the left-hand suture knot 490 off of the rod intermediate portion 488 and onto the inner rod distal end 440. The sleeve 484 is moved to the left relative to the rod 482 and the instrument inner rod 440 until the left-hand knot 490 is pushed over the bends 460 of the second prongs and is positioned on the second prong first sections 458. As the sleeve is moved to the left, the left-hand end wall 508 of the sleeve engages the right-hand knot 490 and moves this knot leftwardly over the rod intermediate portion 488. Once the left-hand knot 490 is positioned on the first section of the second prongs 456, the sleeve 484 is moved to the right on the rod 482 causing the fingers 504 to pass over the right-hand suture knot. Subsequent movement of the sleeve to the left will then cause the fingers to push the right-hand knot off of the rod and onto the inner rod distal end adjacent the second prong bends 460. This completes loading of suture knots onto the instrument by the magazine 480.

The embodiment of the invention shown in FIGS. 26-30 and described above, and its associated reloading magazine shown in FIG. 31 and described above, are both specifically designed to hold two separate suture knots in preparation for their use in a surgical operation. With minor modifications, i.e. increasing the numbers of pairs of first and second prongs and pairs of grooves and slots in the inner rod distal end, the instrument and its associated magazine can be adapted to accommodate three or more successful suture knots wrapped on the distal end of the inner rod. With each additional, separate suture knot that is to be added to the distal end of the inner rod, the corresponding number of pairs of first and second prongs and axial grooves and slots would be correspondingly increased.

FIGS. 32–37 show a still further embodiment of the knot-tying instrument of the present invention. This instrument operates in substantially the same manner and incorporates many of the component parts of previously described embodiments. As with previous embodiments, this embodiment of the instrument is comprised of an inner rod 512, an outer rod 514, a manual handle 516, an end cap 518 and a coil spring 520 positioned between the handle and end cap. The operation of the instrument is substantially the same as that as previously described embodiments. On manipulation of the handle 516 toward and away from the end cap 518, the inner rod distal end 522 reciprocates toward and away from the outer rod distal end 524.

The differences in the instrument embodiment of FIGS. 32–37 from previous embodiments include a lateral slot 526 provided through the side wall of the inner rod. The lateral slot 526 receives the handle pin 528 and permits the inner rod 512 to rotate through an arc segment relative to the manual handle 516 and the outer rod 514.

Adjacent the inner rod proximal end 528 is a cam opening 530 provided through the inner rod side wall. As seen in FIG. 33, the cam opening 530 has a general trapezoidal shape and is surrounded by a first cam surface 532 that extends axially along the inner rod, a second cam surface 534 that extends both axially and radially relative to the inner rod, a third cam surface 536 that again extends axially parallel to the first cam surface, and a fourth cam surface 538 that extends both axially and laterally. A small pin 540 projects from the interior surface of the outer rod 524 into the cam opening 530. The pin 540 does not extend beyond the interior surface of the inner rod 512 and therefore does not interfere with surgical instruments inserted through the interior bores of the two rods. From observing the configurations of the cam opening 530 and the lateral slot 526 through the side wall of the inner rod, it can be seen that manually reciprocating the inner rod to the left as shown in FIG. 3 will cause the rod to move axially relative to the outer rod as the pin 540 travels along the first cam surface 532. Subsequent to the axial movement, the inner rod moves both axially to the left and also rotates through a small arc segment as the pin 540 travels along the second cam surface 534. The lateral slot 526 that receives the pin from the manual handle 516 enables the inner rod to rotate through the arc segment relative to the outer rod and manual handle.

When the pin 540 has reached the corner in the cam opening between the second cam surface 534 and the third cam surface 536, the axial movement of the inner rod 512 to the left relative to the outer rod 514 is at its limit. At this point in the movement of the inner rod, the inner rod distal end 522 is moved to its maximum extent toward the outer rod distal end 524. In continuing with a complete reciprocation of the inner rod relative to the outer rod, the coil spring 520 now biases the handle 516 and the connected inner rod 512 to the right as viewed in FIG. 33. This causes the pin 540 to move along the third cam surface 536 and causes the inner rod to move linearly relative to the outer rod to the right extending the inner rod distal end 522 from the outer rod distal end 524. As the pin 540 completes its travel along the third cam surface 536 and begins to move along the fourth cam surface 538, the inner rod is caused to rotate back through the arc segment as it continues to move axially to the right. On the completion of the reciprocating movement of the inner rod relative to the outer rod, the pin 540 is positioned again at the corner between the fourth cam surface 538 and the first cam surface 532 as shown in FIG. 33. Therefore, on reciprocation of the manual handle 516 to the left and then to the right as viewed in FIG. 33, the pin 540 travels along all four cam surfaces bounding the cam opening 530 and thereby causes the inner rod 512 to first move axially to the left relative to the outer rod, then to rotate through a small arc segment as it continues to move axially to the left, then to move axially to the right, and finally to rotate back through the same arc segment as the inner rod continues to move axially to the right.

The inner rod distal end 522 has a slot 542 formed therethrough. The configuration of the slot is best seen in FIG. 32. As seen in that drawing figures, the left-hand side 544 of the slot extends axially straight back from the inner rod distal end 522 to the proximal end wall 546 of the slot. From the corner between the slot left side wall 544 and the slot proximal end wall 546, the slot end wall 546 extends axially back toward the inner rod distal end 522 as it extends laterally across the inner rod to the slot right side wall 548. The slot right side wall 548 extends axially from the slot end wall 546 toward the inner rod distal end 522. However, as the slot right side wall 548 approaches the inner rod distal end 522, it curves to the left and then continues axially straight toward the rod distal end forming a cam surface projection 550 at the distal end of the inner rod.

The outer rod has a single prong 552 secured to its interior surface 554 adjacent its distal end 524. As best seen in FIG. 32, the prong 552 is positioned on the outer rod distal end 524 so that it is axially aligned with the slot 542 formed in the inner rod distal end 522. The position of the prong 552 relative to the slot 542 shown in FIG. 32 is with the manual handle 516 in its at rest position biased to the right by the spring 520.

FIG. 34 also shows the relative positions of the prong 552 and the slot 542 in the at rest position of the instrument handle. As seen in FIG. 34, the prong 552 has a first section 556 secured to the outer rod interior surface 554 by welding or other equivalent methods. The prong first section extends axially toward the distal end of the inner rod 522 from the outer rod distal end 524. As the prong first section extends from the outer rod distal end, it also extends radially inwardly through the inner rod slot 542. Once the prong first section 556 has passed through the inner rod slot 542, it then extends axially through the inner rod interior bore 558 to a second section 560 of the prong. As the prong first section leads into the prong second section 560, it bends radially outwardly and extends from the rod interior bore 558 through the inner rod slot 542 to a position outside the slot above the exterior surface of the inner rod. The prong second section 560 then extends through a bend 562 in the prong from which it again extends radially inwardly to a distal end 564 of the prong positioned in the inner rod slot 542.

FIGS. 34–37 illustrate use of the instrument embodiment shown in FIGS. 32 and 33. Prior to use, the inner rod distal end 522 is first loaded with two or more suture knots. The pre-tied suture knots can be part of one continuous length of suture to be used in the operation, or the knots can be pre-tied on separate lengths of suture. A first suture knot 566 and a second suture knot 568 are represented schematically in the drawing figures. As with previous embodiments, any known slip knot or any slip knot yet to be developed may be used with the invention. Furthermore, either of the embodiments of the suture loading magazine described earlier in association with other embodiments of the invention may be employed in loading one or more suture knots onto the inner rod distal end of the instrument shown in FIGS. 32 and 33.

FIG. 34 shows the distal ends of the inner and outer rods and the relative positions with the instrument handle in its at rest position biased to the right or toward the distal end of the instrument by the coil spring. In use of the instrument in tying a suture knot, the free end of the suture leading from the first knot 566 is first passed through a stitch in tissue or around a tissue to be ligated and is then drawn back through the inner rod interior bore 558 by a surgical grasper or other type of instrument in the same manner as described earlier with reference to earlier embodiments of the invention. With the free end of the suture passing through the inner rod interior bore, it is then necessary to dispense one or more knots off the end of the instrument to create a one or two throw knot on the length of suture. To dispense the first knot 566 off the inner rod distal end 522, the manual handle 516 is manipulated against the bias of the coil spring 520 and moved toward the instrument proximal end or to the left as shown in FIG. 32. This causes the pin 540 in the interior of the instrument to travel relative to the inner rod 512 along the first cam surface 532. As the inner rod 512 is reciprocated in the outer rod 514 and the inner rod distal end 522 moves toward the outer rod distal end 524, the prong distal end 564 pushes the first knot 566 before it and off of the inner rod distal end 522 as shown in FIG. 35. This first knot 566 may then be moved along the free end of the suture (not shown) extending from the stitch or ligature site up through the rod interior bore 558. The first knot 566 is passed down along the free length of suture and pulled tight at the stitch or ligature site, thereby forming the first throw of a knot. It should also be noticed that as the inner rod distal end 522 moves toward the outer rod distal end 524 while dispensing the first knot 566 off of the inner rod distal end, the outer rod distal end 524 pushes the second knot 568 along the inner rod distal end 522 toward the position previously occupied on the inner rod distal end by the first knot.

As the manual handle 516 is continued to be pulled toward the instrument proximal end, the first cam surface 532 disengages from the pin 540 in the interior of the instrument and the second cam surface 534 then engages the pin. As the second cam surface 534 passes along the pin 540 as the inner rod is continued to be retracted into the outer rod, the configuration of the second cam surface causes the inner rod to rotate through an arc segment relative to the outer rod as it continues to move to the left as shown in FIG. 33. The lateral slot 526 through which the pin 570 of the handle 516 passes permits the rotation of the inner rod relative to the outer rod and the handle. On viewing the instrument from its distal end, the rotation of the inner rod relative to the outer rod is clockwise. This rotation of the inner rod causes the cam surface projection 550 on the distal end of the inner rod to pass over the first section 566 of the outer rod prong 552. As the movement of the second cam surface 534 along the pin 540 comes to completion and the pin 540 nests in the corner between the second cam surface 534 and the third cam surface 536, the reciprocating movement of the inner rod into the outer rod is completed and the inner rod cam surface projection 550 passes over the prong first section 556 to its position relative to the prong shown in FIG. 36. It should also be noted that in this relative position of the inner rod relative to the outer rod, the second knot 568 has now been pushed to the position on the inner rod distal end 522 previously occupied by the first knot 566.

On the return reciprocating stroke of the inner rod relative to the outer rod, the spring 520 biases the handle 516 to the right as viewed in FIG. 33. This causes the inner rod distal end 522 to extend from the outer rod distal end 524 and also causes the third cam surface 536 to move along the pin 540 in the interior of the instrument. As the third cam surface 536 moves along the pin 540, the inner rod moves linearly to the right relative to the outer rod and does not rotate relative to the outer rod. This movement of the inner rod causes the cam surface projection 550 to pass over the prong second section 560 deflecting that section into the inner rod interior bore 558 as shown in FIG. 37. As the movement of the third cam surface 536 comes to its completion with the pin 540 coming to the corner between the third cam surface 536 and the fourth cam surface 538, the inner rod cam surface projection 550 passes completely over the prong second section 560 and the resiliency of the prong causes it to move radially outwardly and emerge from the interior bore 558 of the inner rod resuming its position in the slot 542 on the proximal side of the cam surface projection 550.

As the inner rod 512 continues to move toward its at rest position extended from the outer rod distal end, the fourth cam surface 538 passes along the pin 540 in the interior of the instrument. The engagement of the fourth cam surface 538 with the pin 540 as the inner rod continues to move to the right as viewed in FIG. 33 causes the inner rod to rotate counterclockwise back through the arc segment. On completion of the reciprocating movement of the inner rod relative to the outer rod, the pin 540 again occupies its position between the fourth cam surface 538 and the first cam surface 532 shown in FIG. 33 and the prong 552 occupies its position relative to the slot 542 shown in FIG. 32. The second knot 568 has now been moved to the distal end of the inner rod 522 in a position where it is ready to be dispensed on the next reciprocating movement of the inner rod relative to the outer rod.

While the present invention has been described by reference to a specific embodiment, it should be understood that modifications and variations of the invention may be constructed without departing from the scope of the invention defined in the following claims.

What is claimed:

1. A surgical instrument for tying a knot in a length of suture, the instrument comprising:

an outer rod having a longitudinal length with opposite distal and proximal ends and a hollow interior bore extending therethrough;

an inner rod having a longitudinal length with opposite distal and proximal ends and an interior bore extending therethrough, the inner rod is mounted in the interior bore of the outer rod and has a connection to the outer rod that permits limited longitudinal reciprocating movement of the inner rod relative to the outer rod between an extended position of the inner rod relative to the outer rod where a portion of an exterior surface of the inner rod adjacent the inner rod distal end projects from the outer rod interior bore at the outer rod distal end, and a retracted position of the inner rod relative to the outer rod where the portion of the inner rod exterior surface is retracted into the outer rod interior bore, the portion of the inner rod exterior surface providing a surface for a length of suture to be wrapped in a pattern of loops thereon with the inner rod in the extended position relative to the outer rod, and the portion of the inner rod exterior surface providing a surface which maintains the length of suture in the pattern of wrapped loops as the pattern of loops is slipped over the exterior surface and off the inner rod distal end by the outer rod distal end in response to the inner rod moving from the extended position to the retracted position;

an elongate filament passing through the interior bore of the inner rod, the filament having opposite proximal and distal ends that extend from the opposite proximal and distal ends of the inner rod, respectively;

the distal end of the filament has a connector thereon configured to releasably hold a length of suture; and a length of suture is wrapped in a pattern of loops on the portion of the inner rod exterior surface, and a distal end of the length of suture extends from the pattern of loops and is held by the connector on the filament distal end.

2. The instrument of claim 1, wherein:

the connector is a slot formed in the distal end of the filament that is sufficiently small to hold the length of suture wedged in the slot.

3. The instrument of claim 1, wherein:

the distal end of the filament is extendable from the distal end of the inner rod by pushing the proximal end of the filament into the interior bore of the inner rod at the inner rod proximal end, and the distal end of the filament is retracted into the inner rod interior bore at the distal end of the inner rod by pulling the proximal end of the filament from the inner rod interior bore at the proximal end of the inner rod.

4. The instrument of claim 3, wherein:

the filament is constructed of a flexible, resilient material and has a curved configuration formed in a portion of the filament adjacent its distal end, retracting the distal end of the filament into the inner rod interior bore at the inner rod distal end straightens the curved configuration and extending the filament distal end from the inner rod interior bore at the inner rod distal end causes the portion of the filament to return to its curved configuration.

5. The instrument of claim 1, wherein:

the inner rod has an interior wall extending through its interior bore dividing the interior bore into a first interior bore and a second interior bore, the filament extends through the first interior bore and the second interior bore has a larger cross-sectional area than the first interior bore.

6. The instrument of claim 5, wherein:

the interior wall has a flat surface opposing the filament and the filament has a flat surface opposing the interior wall flat surface and the mutually opposing flat surfaces of the filament and the interior wall prevent the filament from rotating in the first interior bore.

7. A surgical instrument for tying a knot in a length of suture, the instrument comprising:

an outer rod having a longitudinal length with opposite distal and proximal ends and a hollow interior bore extending therethrough;

an inner rod having a longitudinal length with opposite distal and proximal ends and an interior bore extending therethrough, the inner rod is mounted in the outer rod interior bore for longitudinal reciprocating movement of the inner rod relative to the outer rod between an extended position of the inner rod relative to the outer rod where a portion of an exterior surface of the inner rod adjacent the inner rod distal end projects from the outer rod interior bore at the outer rod distal end, and a retracted position of the inner rod relative to the outer rod where the portion of the inner rod exterior surface is retracted into the outer rod interior bore;

a length of suture wrapped in a pattern of loops on the portion of the inner rod exterior surface, the length of suture having a distal end that extends from the pattern of loops;

an elongate filament passing through the inner rod interior bore, the filament having opposite proximal and distal ends that extend from the opposite proximal and distal ends of the inner rod, respectively, the distal end of the filament having a connector thereon that releasably holds the length of suture distal end; and the inner rod has an interior wall extending through its interior bore dividing the interior bore into a first interior bore and a second interior bore, the filament extends through the first interior bore and the second interior bore has a larger cross-sectional area than the first interior bore.

8. The instrument of claim 7, wherein:

the inner rod has a connection to the outer rod that permits only limited longitudinal reciprocating movement of the inner rod relative to the outer rod.

9. The instrument of claim 7, wherein:

the connector is a slot formed in the filament distal end and the length of suture distal end is wedged in the slot.

10. The instrument of claim 7, wherein:

the distal end of the filament is extendable from the distal end of the inner rod by pushing the proximal end of the filament into the interior bore of the inner rod at the inner rod proximal end, and the distal end of the filament is retracted into the inner rod interior bore at the distal end of the inner rod by pulling the proximal end of the filament from the inner rod interior bore at the proximal end of the inner rod.

11. The instrument of claim 10, wherein:

the filament is constructed of a flexible, resilient material and has a curved configuration formed in a portion of the filament adjacent its distal end, retracting the distal end of the filament into the inner rod interior bore at the inner rod distal end straightens the curved configuration and extending the filament distal end from the inner rod interior bore at the inner rod distal end causes the portion of the filament to return to its curved configuration.

12. The instrument of claim 7, wherein:

the interior wall has a flat surface opposing the filament and the filament has a flat surface opposing the interior wall flat surface and the mutually opposing flat surfaces of the filament and the interior wall prevent the filament from rotating in the first interior bore.

13. A surgical instrument for tying a knot in a length of suture, the instrument comprising:

a rod having a longitudinal length with opposite distal and proximal ends and a hollow interior bore extending therethrough, an interior wall extends through the rod interior bore dividing the interior bore into a first interior bore and a second interior bore, the interior wall has a flat surface facing the first interior bore;

an elongate filament passing through the first interior bore, the filament having opposite proximal and distal ends that extend from the opposite proximal and distal ends of the first interior bore, the distal end of the filament having a connector thereon configured to releasably hold a length of suture, the distal end of the filament is extendable from the distal end of the rod by pushing the proximal end of the filament into the first interior bore at the rod proximal end, the distal end of the filament is retractable into the first interior bore at the rod distal end by pulling the filament proximal end from the first interior bore at the rod proximal end, and the filament has a flat surface opposing the interior wall flat surface with the mutually opposing flat surfaces of the filament and interior wall preventing the filament from rotating in the first interior bore.

14. The instrument of claim 13, wherein:

the filament is constructed of a flexible, resilient material and has a curved configuration formed in a portion of the filament adjacent its distal end, retracting the distal end of the filament into the first interior bore at the rod distal end straightens the curved configuration and extending the filament distal end from the first interior bore at the rod distal end causes the portion of the filament to return to its curved configuration.

15. The instrument of claim 14, wherein:

a length of suture is wrapped in a pattern of loops on a portion of an exterior surface of the rod adjacent the rod distal end and the length of suture has a distal end that extends from the pattern of loops and is held by the connector on the filament distal end.

16. The instrument of claim 15, wherein:

the connector on the filament distal end is a slot and the suture distal end is wedged in the slot.

17. The instrument of claim 15, wherein:

the rod is an inner rod mounted in an interior bore of an outer rod, the outer rod has a longitudinal length with opposite distal and proximal ends and the inner rod is mounted in the outer rod for longitudinal reciprocating movement of the inner rod relative to the outer rod.

18. The instrument of claim 17, wherein:

the inner rod has a connection to the outer rod that permits only limited longitudinal reciprocating movement of the inner rod relative to the outer rod.

* * * * *